US011096916B2

(12) United States Patent
Di Paolo et al.

(10) Patent No.: US 11,096,916 B2
(45) Date of Patent: *Aug. 24, 2021

(54) USE OF NICOTINIC ACETYLCHOLINE RECEPTOR ALPHA 7 ACTIVATORS

(71) Applicant: NOVARTIS AG, Basel (CH)

(72) Inventors: Therese Di Paolo, Quebec (CA); Dominik Feuerbach, Basel (CH); Baltazar Gomez-Mancilla, Basel (CH); Donald Johns, Woburn, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/703,501

(22) Filed: Dec. 4, 2019

(65) Prior Publication Data
US 2020/0108035 A1 Apr. 9, 2020

Related U.S. Application Data

(63) Continuation of application No. 13/393,351, filed as application No. PCT/EP2010/063946 on Sep. 22, 2010, now Pat. No. 10,537,539.

(60) Provisional application No. 61/244,658, filed on Sep. 22, 2009.

(51) Int. Cl.
A61K 31/198 (2006.01)
A61K 31/444 (2006.01)
A61K 45/06 (2006.01)

(52) U.S. Cl.
CPC ............ *A61K 31/198* (2013.01); *A61K 45/06* (2013.01)

(58) Field of Classification Search
CPC .. A61K 31/198; A61K 45/06; A61K 2121/00; A61P 43/00; A61P 25/16; A61P 25/14
See application file for complete search history.

(56) References Cited

U.S. PATENT DOCUMENTS

| | | |
|---|---|---|
| 2002/0016370 A1 | 2/2002 | Shytle |
| 2003/0045523 A1 | 3/2003 | Schmitt |
| 2003/0073715 A1 | 4/2003 | El-Rashidy |
| 2003/0119840 A1 | 6/2003 | Galli |
| 2003/0166654 A1 | 9/2003 | Nozulak |
| 2004/0229868 A1 | 11/2004 | Herbert |
| 2005/0154045 A1 | 7/2005 | Luithle |
| 2005/0165005 A1 | 7/2005 | Genevois-Borella |
| 2005/0209236 A1 | 9/2005 | Hendrix |
| 2006/0106096 A1 | 5/2006 | Flessner |
| 2006/0292604 A1 | 12/2006 | Pulst |
| 2007/0037844 A1 | 2/2007 | Luithle |
| 2007/0254921 A1 | 11/2007 | Sellers et al. |
| 2008/0096891 A1 | 4/2008 | Benedetti |
| 2009/0088418 A1 | 4/2009 | Pfister |
| 2009/0143424 A1 | 6/2009 | Crooks |
| 2009/0181984 A1 | 7/2009 | Peters |
| 2012/0157464 A1 | 6/2012 | Feuerbach et al. |

FOREIGN PATENT DOCUMENTS

| | | | |
|---|---|---|---|
| CN | 1678611 A | 10/2005 | |
| CN | 1984911 A | 6/2007 | |
| CN | 101039670 A | 9/2007 | |
| CN | 101268071 A | 9/2008 | |
| CN | 101305003 A | 11/2008 | |
| EP | 1 977 746 A1 | 10/2008 | |
| EP | 1977746 A1 * | 10/2008 | ........... A61K 31/465 |
| JP | 2004-534065 A | 11/2004 | |
| WO | WO 97/39754 A1 | 10/1997 | |
| WO | WO 01/85727 A1 | 11/2001 | |
| WO | WO 02/100858 A2 | 12/2002 | |
| WO | WO 03/043991 A1 | 5/2003 | |
| WO | 03047581 A1 | 6/2003 | |
| WO | WO 03/078430 A1 | 9/2003 | |
| WO | WO 03/078431 A1 | 9/2003 | |
| WO | 2004000316 A1 | 12/2003 | |
| WO | 2004016608 A1 | 2/2004 | |
| WO | WO 2004/013136 A1 | 2/2004 | |
| WO | WO 2004/019943 A1 | 3/2004 | |
| WO | WO 2004/022556 A1 | 3/2004 | |
| WO | WO-2004022556 A1 * | 3/2004 | .............. A61P 25/22 |
| WO | WO 2004/029050 A1 | 4/2004 | |
| WO | WO 2004/074245 A2 | 9/2004 | |
| WO | WO 2004/076449 A2 | 9/2004 | |
| WO | WO 2004/076453 A1 | 9/2004 | |
| WO | WO 2004/108668 A2 | 12/2004 | |
| WO | WO 2005/028477 A1 | 3/2005 | |
| WO | 2005044265 A1 | 5/2005 | |
| WO | 2005044266 A1 | 5/2005 | |
| WO | 2005044267 A1 | 5/2005 | |
| WO | WO 2005/063767 A2 | 7/2005 | |

(Continued)

OTHER PUBLICATIONS

Maryka Quik, Luping Z. Huang, Neeraja Parameswaran, Tanuja Bordia, Carla Campos, Xiomara A. Perez, Multiple roles for nicotine in Parkinson's disease, Biochemical Pharmacology 78 (2009) 677-685 (Year: 2009).*
Michael J. Fox Foundation webpage (Year: 2008).*
Mihalak KB, Carroll FI, Luetje CW., Varenicline is a partial agonist at alpha4beta2 and a full agonist at alpha7 neuronal nicotinic receptors, Mol Pharmacol. Sep. 2006;70(3):801-5. Epub Jun. 9, 2006 (Year: 2006).*
Michael J. Fox Foundation webpage copy, dated 2008, retrieved Jan. 22, 2018 (Year: 2008).
Arias et al., "Different Interaction between the Agonist JN403 and the Competitive Antagonist Methyllycaconitine with the Human a7 Nicotinic Acetylcholine Receptor," Biochemistry, vol. 49, No. 19 (2010), pp. 4169-4180.

(Continued)

Primary Examiner — Sarah Pihonak
Assistant Examiner — Jason Deck
(74) Attorney, Agent, or Firm — Hoffman Warnick LLC

(57) ABSTRACT

The invention concerns the use of a nicotinic acetylcholine receptor alpha 7 activators for the treatment, prevention or delay of progression of dyskinesia associated with dopamine agonist therapy in Parkinson's Disease.

6 Claims, 4 Drawing Sheets

(56) References Cited

FOREIGN PATENT DOCUMENTS

| WO | WO 2005/074940 A1 | 8/2005 |
|---|---|---|
| WO | WO 2005/075482 A1 | 8/2005 |
| WO | 2005079802 A1 | 9/2005 |
| WO | WO 2005/092890 A2 | 10/2005 |
| WO | WO 2005/111033 A2 | 11/2005 |
| WO | WO 2005/111038 A2 | 11/2005 |
| WO | WO 2005/118535 A1 | 12/2005 |
| WO | WO 2005/123732 A1 | 12/2005 |
| WO | WO 2006/001894 A1 | 1/2006 |
| WO | WO 2006/005608 A1 | 1/2006 |
| WO | WO 2006/040352 A1 | 4/2006 |
| WO | WO 2006/048294 A1 | 5/2006 |
| WO | WO 2006/051394 A1 | 5/2006 |
| WO | WO 2006/051407 A1 | 5/2006 |
| WO | WO 2006/058879 A1 | 6/2006 |
| WO | WO 2006/065233 A1 | 6/2006 |
| WO | WO 2006/067611 A1 | 6/2006 |
| WO | WO 2006/069097 A2 | 6/2006 |
| WO | WO 2006/087306 A2 | 8/2006 |
| WO | WO 2006/103511 A1 | 10/2006 |
| WO | WO 2006/111662 A2 | 10/2006 |
| WO | 2006114262 A1 | 11/2006 |
| WO | WO 2007/018738 A2 | 2/2007 |
| WO | WO 2007/038367 A1 | 4/2007 |
| WO | WO 2007/045478 A1 | 4/2007 |
| WO | WO 2007/056582 A1 | 5/2007 |
| WO | 2007071358 A1 | 6/2007 |
| WO | WO 2007/065892 A1 | 6/2007 |
| WO | WO 2007/068475 A1 | 6/2007 |
| WO | WO 2007/068476 A1 | 6/2007 |
| WO | WO 2007/085036 A1 | 8/2007 |
| WO | WO 2007/089626 A2 | 8/2007 |
| WO | WO 2007/093600 A1 | 8/2007 |
| WO | WO 2007/095728 A1 | 8/2007 |
| WO | WO 2007/098418 A1 | 8/2007 |
| WO | WO 2007/110730 A2 | 10/2007 |
| WO | WO 2007/133155 A1 | 11/2007 |
| WO | WO 2007/135121 A1 | 11/2007 |
| WO | WO 2007/135122 A1 | 11/2007 |
| WO | WO 2007/138037 A1 | 12/2007 |
| WO | WO 2007/146066 A2 | 12/2007 |
| WO | WO 2007/149163 A2 | 12/2007 |
| WO | WO 2008/010073 A1 | 1/2008 |
| WO | WO 2008/058096 A2 | 5/2008 |
| WO | WO 2008/087529 A1 | 7/2008 |
| WO | WO 2008/101247 A2 | 8/2008 |
| WO | WO 2008/122049 A2 | 10/2008 |
| WO | WO 2008/147812 A2 | 12/2008 |
| WO | WO 2009/018505 A1 | 2/2009 |
| WO | WO 2009/023844 A2 | 2/2009 |
| WO | WO 2009/043780 A1 | 4/2009 |
| WO | WO 2009/043784 A1 | 4/2009 |
| WO | WO 2009/066107 A1 | 5/2009 |
| WO | WO 2009/098576 A1 | 8/2009 |
| WO | WO 2009/105585 A2 | 8/2009 |
| WO | WO 2009/127678 A1 | 10/2009 |
| WO | WO 2009/128058 A1 | 10/2009 |
| WO | WO 2009/143019 A2 | 11/2009 |
| WO | WO 2009/146031 A1 | 12/2009 |
| WO | WO 2010/002802 A1 | 1/2010 |
| WO | WO 2010/008832 A1 | 1/2010 |
| WO | WO 2010/011546 A2 | 1/2010 |
| WO | WO 2010/021797 A1 | 2/2010 |
| WO | WO 2010/024980 A1 | 3/2010 |
| WO | WO 2010/043515 A1 | 4/2010 |
| WO | WO 2010/056622 A1 | 5/2010 |
| WO | WO 2010/085724 A1 | 7/2010 |
| WO | WO 2010/147938 A2 | 12/2010 |

OTHER PUBLICATIONS

Office Action and English Translation thereof for Japanese Patent Application No. 2015-237921 dated Nov. 19, 2016, 7 pages.

Office Action and English Translation thereof for Chinese Patent Application No. 201080042255.4 dated Oct. 20, 2016, 6 pages.

Notice of Allowance and Search Report with English Translation thereof for Taiwanese Patent Application No. 099132066 dated Sep. 20, 2016, 7 pages.

Office Action and English Translation thereof for Korean Patent Application No. 10-2012-7007287 dated Dec. 14, 2016, 20 pages.

Office Action and English Translation thereof for Japanese Patent Application No. 2012-530248 dated Nov. 8, 2016, 9 pages.

Abstract for Taiwanese Patent Application No. 094145327 dated Dec. 20, 2005, retrieved from http://twpat6.tipo.gov.tw/tipotwoc/tipotwekm?0006E24E00020105 . . . on Apr. 29, 2014, 1 page.

Office Action and English Translation thereof for Taiwanese Patent Application No. 099132066 dated Apr. 21, 2014, 9 pages.

Office Action and English Translation thereof for Taiwanese Patent Application No. 099132066 dated Jan. 16, 2015, 12 pages.

Gronlien et al., "Distinct profiles of alpha7 nAChR positive allosteric modulation revealed by structurally diverse chemotypes," Mol Pharmacol. 72(3):715-24 (2007). Abstract provided.

Office Action for Taiwanese Application No. 099132066, dated Nov. 17, 2015, 7 pages.

Tuesta et al., "Recent advances in understanding nicotinic receptor signaling mechanisms that regulate drug self-administration behavior," Biochemical Pharmacology. 82:984-95 (2011). Author Manuscript provided.

Quik M et al., Multiple roles for nicotine in Parkinson's disease, Biochemical Pharmacology, vol. 78, No. 7 (2009), pp. 677-685.

Feuerbach, U.S. PTO Office Action, U.S. Appl. No. 13/383,690, dated May 28, 2014, 23 pgs.

Feuerbach, U.S. PTO Restriction Requirement, U.S. Appl. No. 13/383,690, dated Aug. 23, 2013, 6 pgs.

English translation of Chinese Office Action, Appl. No. 201080042255.4, dated Feb. 5, 2013, 5 pgs.

Chavez-Noriega et al., "Pharmacological Characterization of Recombinant Human Neuronal Nicotinic Acetylcholine Receptors hα2β2, hα2β4, hα3β2, hα3β4, hα4β2, hα4β4 and hα7 Expressed in *Xenopus* Oocytes", The Journal of Pharmacology and Experimental Therapeutics, vol. 280, No. 1 (1997), pp. 346-356.

Huang et al., "Nicotinic receptor agonists decrease L-dopa-induced dyskinesias most effectively in partially lesioned parkinsonian rats", Neuropharmacology, vol. 60 (2011), pp. 861-868.

Lexicon of psychiatry, neurology and the neurosciences, Frank, J. Ayd, Jr.—$2^{nd}$ ed. (2000), pp. 964-965.

U.S. Appl. No. 13/383,690, filed Feb. 27, 2012, Feuerbach et al.

Abin-Carriquiry et al., "Increase in locomotor activity after acute administration of the nicotinic receptor agonist 3-bromocytisine in rats", European Journal of Pharmacology, vol. 634 (2010), pp. 89-94.

Al-Rejaie et al., "Behavioral Interaction Between Nicotine and Ethanol: Possible Modulation by Mouse Cerebellar Glutamate", Alcoholism: Clinical and Experimental Research, vol. 30, No. 7 (2006), pp. 1223-1233.

Arias et al., "Different Interaction between the Agonist JN403 and the Competitive Antagonist Methyllycaconitine with the Human α7 Nicotinic Acetylcholine Receptor", Biochemistry, vol. 49, No. 19 (2010), pp. 4169-4180.

Banerjee et al., "Cellular Expression of α7 Nicotinic Acetylcholine Receptor Protein in the Temporal Cortex in Alzheimer's and Parkinson's Disease—A Stereological Approach", Neurobiology of Disease, vol. 7 (2000), pp. 666-672.

Bordia et al., "Partial Recovery of Striatal Nicotinic Receptors in 1-Methyl-4-phenyl-1,2,3,6-tetrahydropyridine (MPTP)-Lesioned Monkeys with Chronic Oral Nicotine", The Journal of Pharmacology & Experimental Therapeutics, vol. 319, No. 1 (2006), pp. 285-292.

Broad et al., "Selective α7 nicotinic acetylcholine receptor ligands for the treatment of neuropsychiatric diseases", Drugs of the Future, vol. 32, No. 2 (2007), pp. 161-170.

Brown et al., "Recent advances in the treatment of L-DOPA-induced dyskinesia", Idrugs, vol. 5, No. 5, (2002), pp. 454-468.

Calabresi et al., "A convergent model for cognitive dysfunctions in Parkinson's disease: the critical dopamine-acetylcholine synaptic balance", Lancet Neurol, vol. 5 (2006), pp. 974-983.

(56) References Cited

OTHER PUBLICATIONS

Campos et al., "In vivo modulation of α7 nicotinic receptors on striatal glutamate release induced by anatoxin-A", Neurochemistry International, vol. 56 (2010), pp. 850-855.
Carrillo-Mora et al., "Protective effect of systemic L-kynurenine and probenecid administration on behavioural and morphological alterations induced by toxic soluble amyloid beta (25-35) in rat hippocampus", Behavioural Brain Research, vol. 210 (2010), pp. 240-250.
Chen et al., "Smoking duration, Intensity, and risk of Parkinson disease", Neurology, vol. 74 (2010), pp. 878-884.
Chilton et al., Behavioral consequences of methyliycaconitine in mice: a model of α7 nicotinic acetylcholine receptor deficiency, Life Sciences, vol. 74 (2004), pp. 3133-3139.
Cincotta et al., "Selective nicotinic acetylcholine receptor agonists: Potential therapies for neuropsychiatric disorders with cognitive dysfunction", Current Opinion in Investigational Drugs, vol. 9, No. 1 (2008), pp. 47-56.
Fabbrini et al., "Levodopa-Induced Dyskinesias", Movement Disorders, vol. 22, No. 10 (2007), pp. 1379-1389.
Fernandez et al., "Insulin-like growth factor I restores motor coordination in a rat model of cerebellar ataxia", Proc. Natl. Acad. Sci. USA, vol. 95 (1998), pp. 1253-1258.
Fernandez-Gonzalez et al., "Purkinje cell degeneration (pcd) Phenotypes Caused by Mutations in the Axotomy-Induced Gene, Nna1", Science, vol. 295 (2002), pp. 1904-1906.
Feuerbach et al., "Coupling of human nicotinic acetylcholine receptors α7 to calcium channels in GH3 cells", Neuropharmacology, vol. 48 (2005), pp. 215-227.
Feuerbach et al., "JN403, in vitro characterization of a novel nicotinic acetylcholine receptor α7 selective agonist", Neuroscience Letters, vol. 416 (2007), pp. 61-65.
Feuerbach et al., "The selective nicotinic acetylcholine receptor α7 agonist JN403 is active in animal models of cognition, sensory gating, epilepsy and pain", Neuropharmacology, vol. 56 (2009), pp. 254-263.
Finberg et al., "Cardiovascular responses to combined treatment with selective monoamine oxidase type B inhibitors and L-DOPA in the rat", British Journal of Pharmacology, vol. 149, No. 6 (2006), pp. 647-656.
Fogel et al., "Clinical features and molecular genetics of autosomal recessive cerebellar ataxias", Lancet Neurol, vol. 6 (2007), pp. 245-257.
Ghiron et al., "Novel Alpha-7 Nicotinic Acetylcholine Receptor Agonists Containing a Urea Moiety: Identification and Characterizaton of the Potent, Selective, and Orally Efficacious Agonist 1-[6-(4-Fluorophenyl)pyridin-3-yl]-3-(4-piperidin-1-ylbutyl)Urea(SEN34625/WYE-103914)", J. Med. Chem., vol. 53 (2010), pp. 4379-4389.
Greégoire et al., "Prolonged kynurenine 3-hydroxylase inhibition reduces development of levodopa-induced dyskinesias in parkinsonian monkeys", Behavioural Brain Research, vol. 186 (2008), pp. 161-167.
Hadj Tahar et al., "Sustained Cabergoline Treatment Reverses Levodopa-Induced Dyskinesias in Parkinsonian Monkeys", Clinical Neuropharmacology, vol. 23, No. 4 (2000), pp. 195-202.
Haydar et al., "Neuronal Nicotinic Acetylcholine Receptors—Targets for the Development of Drugs to Treat Cognitive Impairment Associated with Schizophrenia and Alzheimer's Disease", Current Topics in Medicinal Chemistry, vol. 10 (2010), pp. 144-152.
Honti et al., "Genetic and molecular aspects of spinocerebellar ataxias", Neuropsychiatric Disease & Treatment, vol. 1, No. 2 (2005), pp. 125-133.
Horenstein et al., "Multiple Pharmacophores for the Selective Activation of Nicotinic α7-Type Acetylcholine Receptors", Molecular Pharmacology, vol. 74 (2008), pp. 1496-1511.
International Preliminary Report on Patentability, PCT/EP2010/060571, dated Jan. 24, 2012, 12 pgs.
International Preliminary Report on Patentability, PCT/EP2010/063946, dated Mar. 27, 2012, 7 pgs.
International Search Report, PCT/EP2010/060571, dated Aug. 10, 2011, 9 pgs.
International Search Report, PCT/EP2010/063946, dated Jan. 12, 2011, 5 pgs.
Klockgether, "Ataxias", Parkinsonism & Related Disorders, vol. 13 (2007), pp. S391-S394.
Konitsiotis, "Novel pharmacological strategies for motor complications in Parkinson's disease", Expert Opin. Investig. Drugs, vol. 14, No. 4 (2005), pp. 377-392.
Kulak et al., "Differences in α7 nicotinic acetylcholine receptor binding in motor symptomatic and asymptomatic MPTP-treated monkeys", Brain Research, vol. 999 (2004), pp. 193-202.
Martin-Ruiz et al., "Alpha and beta nicotinic acetylcholine receptors subunits and synaptophysin in putamen from Parkinson's disease", Neuropharmacology, vol. 39 (2002), pp. 2830-2839.
Mascalchi, "Spinocerebellar ataxias", Neurol Sci, vol. 29 (2008), pp. S311-S313.
Messi et al., "Activation of α7 nicotinic acetylcholine receptor promotes survival of spinal cord motoneurons", FEBS Letters. vol. 411 (1997), pp. 32-38.
Michelmore et al., "Study of the calcium dynamics of the human α4β2, α3β4 and α1β1γδ nicotinic acetylcholine receptors", Naunyn-Schmiedeberg's Arch Pharmacol, vol. 366 (2002), pp. 235-245.
Nguyen et al., "Autoradiographic Analysis of [125I]Alpha-Bungarotoxin Bindings in Discrete Brain Regions of Weaver Mice", Neuroscience 2001 Meeting Abstract, Presentation No. 596.7.
O'Donnell et al., "Discovery of 4-(5-Methyloxazolo[5,5-b]pyridin-2-yl0-1,4-diazabicyclo[3.2.2]nonane (CP-810, 123), a Novel α7 Nicotinic Acetylcholine Receptor Agonist for the Treatment of Cognitive Disorders in Schizophrenia: Synthesis, SAR Development, and in Vivo Efficacy in Cognition Models", J. Med. Chem., vol. 53 (2010), pp. 1222-1237.
Quattara et al., Implication of NMDA Receptors in the Antidyskinetic Activity of Cabergoline, CI-1041, and Ro 61-8048 in MPTP Monkeys with Levodopa-induced Dyskinesias, J Mol Neurosci, vol. 38 (2009), pp. 128-142.
Quik et al., "Nicotine Reduces Levodopa-induced Dyskinesias in Lesioned Monkeys", Annals of Neurology, vol. 62, No. 6 (2007), pp. 588-596.
Quik et al., "Nicotinic receptors as CNS targets for Parkinson's disease", Biochemical Pharmacology, vol. 74 (2007), pp. 1224-1234.
Quik M et al., "nAChR agonists reduce L-dopa-induced dyskinesias in parkinsonian rats", Biochemical Pharmacology, vol. 78, No. 7 (2009), p. 922.
Rollema et al., "Preclinical pharmacology of the α4β2 nAChR partial agonist varenicline related to effects on reward, mood and cognition", Biochemical Pharmacology, vol. 78 (2009), pp. 813-824.
Romanelli et al., "The quest for the treatment of cognitive impairment: α7 nicotinic and α5 GABAA receptor modulators", Expert Opin. Ther. Patents, vol. 17, No. 11 (2007), pp. 1365-1377.
Samadi et al., "Effect of Kynurenine 3-Hydroxylase Inhibition on the Dyskinetic and Antiparkinsonian Responses to Levodopa in Parkinsonian Monkeys", Movement Disorders, vol. 20, No. 7 (2005), pp. 792-802.
Samadi et al., "Opioid antagonists increase the dyskinetic response to dopaminergic agents in parkinsonian monkeys: Interaction between dopamine and opioid systems", Neuropharmacology, vol. 45 (2003), pp. 954-963.
Smith et al., "Mouse cerebellar nicotinic-cholinergic receptor modulation of Δ9-THC ataxia: Role of the α4β2 subtype", Brain Research, vol. 1115 (2006), pp. 16-25.
Tamim et al., "Effect of non-dopaminergic drug treatment on Levodopa induced dyskinesias in MPTP monkeys: Common Implication of striatal neuropeptides", Neuropharmacology, vol. 58 (2010), pp. 286-296.
Zesiewicz et al., "Treatment of Ataxia and Imbalance With Varenicline (Chantix): Report of 2 Patients with Spinocerebellar Ataxia (Types 3 and 14)", Clinical Neuropharmacology, vol. 31, No. 6 (Nov./Dec. 2008), pp. 363-365.

(56) References Cited

OTHER PUBLICATIONS

Zesiewicz et al., "Subjective improvement in proprioception in 2 patients with atypical Friedreich ataxia treated with varenicline (Chantix)", Journal of Clinical Neuromuscular Disease, vol. 10, No. 4 (2009), pp. 191-193.

* cited by examiner

USE OF NICOTINIC ACETYLCHOLINE RECEPTOR ALPHA 7 ACTIVATORS

CROSS REFERENCE TO RELATED APPLICATIONS

The present application is a continuation of U.S. patent application Ser. No. 13/393,351, filed Feb. 29, 2012, which is a US national phase under 35 USC § 371 of International Patent Application No. PCT/EP2010/063946, filed Sep. 22, 2010, which in turn claims the benefit of U.S. Provisional Application No. 61/244,658, filed Sep. 22, 2009.

BACKGROUND

The present invention relates to pharmaceutical uses of nicotinic acetylcholine receptor alpha 7 (α7-nAChR) activators, i.e. α7-nAChR agonists or positive allosteric modulators.

Parkinson's Disease (PD) is a chronic and progressive degenerative disorder of the central nervous system that often impairs the sufferer's motor skills and speech. Characteristics of Parkinson's Disease are varied and include one or more of the following: tremor, rigidity, bradykinesia, akinesia, gait and postural disturbances, postural instability, speech and swallowing disturbances and cognitive impairment (e.g. memory loss, dementia and slowed reaction times). PD is thought to be the direct result of the loss of dopamine-producing cells in the substantia nigra. More than 60,000 new cases of PD are diagnosed in the USA alone each year.

The most commonly used treatment for PD is dopamine agonist therapy, for example by administration of L-dopa (levodopa) in combination with a decarboxylase inhibitor (e.g. carbidopa). However, for many patients, a long term dopamine agonist therapy causes involuntary movements (dyskinesias) as a significant side effect (for review: Fabbrini et al, Movement Disorders, 2007, 22(10), 1379-1389; Konitsiotis, Expert Opin Investig Drugs, 2005, 14(4), 377-392; Brown et al, IDrugs, 2002, 5(5), 454-468). Consequently, there is a need for effective regimes for inhibiting or treating dyskinesia, which can be carried out without adversely affecting anti-PD treatments.

Compounds described as α7-nAChR agonists or α7-nAChR positive allosteric modulators have been described in, e.g. WO2001/85727, WO2004/022556, WO2005/118535, WO2005/123732, WO2006/005608, WO2007/045478, WO2007/068476, WO2007/068475 and Haydar et al (Current Topics in Medicinal Chemistry, 2010, 10, 144-152).

SUMMARY OF INVENTION

It has been found that α7-nAChR agonists or α7-nAChR positive allosteric modulators may be used in the treatment, prevention or delay of progression of dyskinesia associated with dopamine agonist therapy in PD. In particular, it has been found that α7-nAChR agonists or α7-nAChR positive allosteric modulators may be used in the treatment, prevention or delay of progression of said dyskinesia, wherein the therapy comprises the administration of levodopa.

Accordingly, a first aspect of the invention concerns the use of a α7-nAChR agonist or a α7-nAChR positive allosteric modulator for the treatment (whether therapeutic or prophylactic), prevention or delay of progression of dyskinesia associated with dopamine agonist therapy in Parkinson's Disease.

One embodiment of said first aspect concerns the use of a α7-nAChR agonist for the treatment (whether therapeutic or prophylactic), prevention or delay of progression of dyskinesia associated with dopamine agonist therapy in Parkinson's Disease.

Another embodiment of said first aspect concerns the use of a α7-nAChR positive allosteric modulator for the treatment (whether therapeutic or prophylactic), prevention or delay of progression of dyskinesia associated with dopamine agonist therapy in Parkinson's Disease.

A further aspect of the invention relates to a method for the treatment, prevention or delay of progression of dyskinesia associated with dopamine agonist therapy in Parkinson's Disease in a subject in need of such treatment, which comprises administering to said subject a therapeutically effective amount of a α7-nAChR agonist or a α7-nAChR positive allosteric modulator.

One embodiment of said further aspect relates to a method for the treatment, prevention or delay of progression of dyskinesia associated with dopamine agonist therapy in Parkinson's Disease in a subject in need of such treatment, which comprises administering to said subject a therapeutically effective amount of a α7-nAChR agonist. Another embodiment of said further aspect relates to a method for the treatment, prevention or delay of progression of dyskinesia associated with dopamine agonist therapy in Parkinson's Disease in a subject in need of such treatment, which comprises administering to said subject a therapeutically effective amount of a α7-nAChR positive allosteric modulator.

A further aspect of the invention relates to a method for the treatment, prevention or delay of progression of dyskinesia associated with dopamine agonist therapy in Parkinson's Disease in a subject in need of such treatment, which comprises (i) diagnosing dyskinesia associated with dopamine agonist therapy in Parkinson's Disease in said subject and (ii) administering to said subject a therapeutically effective amount of a α7-nAChR agonist or a α7-nAChR positive allosteric modulator.

One embodiment of said further aspect relates to a method for the treatment, prevention or delay of progression of dyskinesia associated with dopamine agonist therapy in Parkinson's Disease in a subject in need of such treatment, which comprises (i) diagnosing dyskinesia associated with dopamine agonist therapy in Parkinson's Disease in said subject and (ii) administering to said subject a therapeutically effective amount of a α7-nAChR agonist.

Another embodiment of said further aspect relates to a method for the treatment, prevention or delay of progression of dyskinesia associated with dopamine agonist therapy in Parkinson's Disease in a subject in need of such treatment, which comprises (i) diagnosing dyskinesia associated with dopamine agonist therapy in Parkinson's Disease in said subject and (ii) administering to said subject a therapeutically effective amount of a α7-nAChR positive allosteric modulator.

A further aspect of the invention relates to a pharmaceutical composition comprising a α7-nAChR agonist or a α7-nAChR positive allosteric modulator for the treatment, prevention or delay of progression of dyskinesia associated with dopamine agonist therapy in Parkinson's Disease.

One embodiment of said further aspect relates to a pharmaceutical composition comprising a α7-nAChR agonist or a α7-nAChR positive allosteric modulator for the treatment, prevention or delay of progression of dyskinesia associated with dopamine agonist therapy in Parkinson's Disease.

Another embodiment of said further aspect relates to a pharmaceutical composition comprising a α7-nAChR agonist or a α7-nAChR positive allosteric modulator for the treatment, prevention or delay of progression of dyskinesia associated with dopamine agonist therapy in Parkinson's Disease.

A further aspect of the invention relates to the use of a α7-nAChR agonist or a α7-nAChR positive allosteric modulator for the manufacture of a medicament for the treatment, prevention or delay of progression of dyskinesia associated with dopamine agonist therapy in Parkinson's Disease.

One embodiment of said further aspect relates to the use of a α7-nAChR agonist for the manufacture of a medicament for the treatment, prevention or delay of progression of dyskinesia associated with dopamine agonist therapy in Parkinson's Disease.

Another embodiment of said further aspect relates to the use of a α7-nAChR positive allosteric modulator for the manufacture of a medicament for the treatment, prevention or delay of progression of dyskinesia associated with dopamine agonist therapy in Parkinson's Disease.

Figure 1:
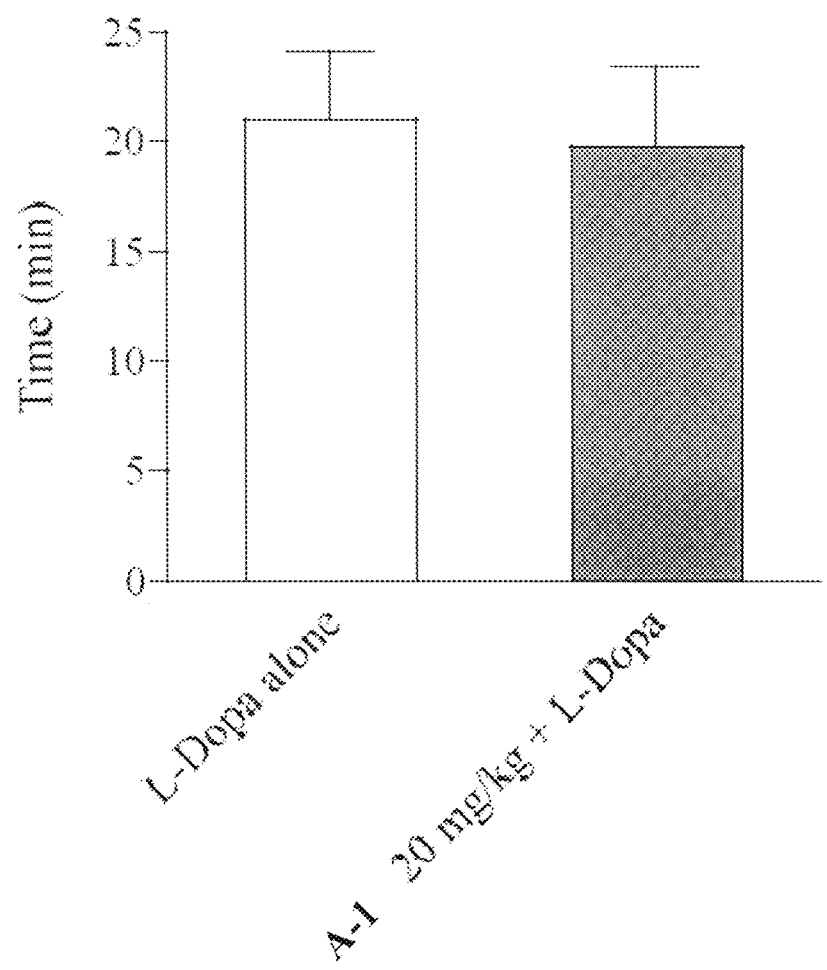
FIG. 1 provides a bar chart showing elapsed time after L-dopa administration for behavioural response in parkinsonian primates.
Figure 2:
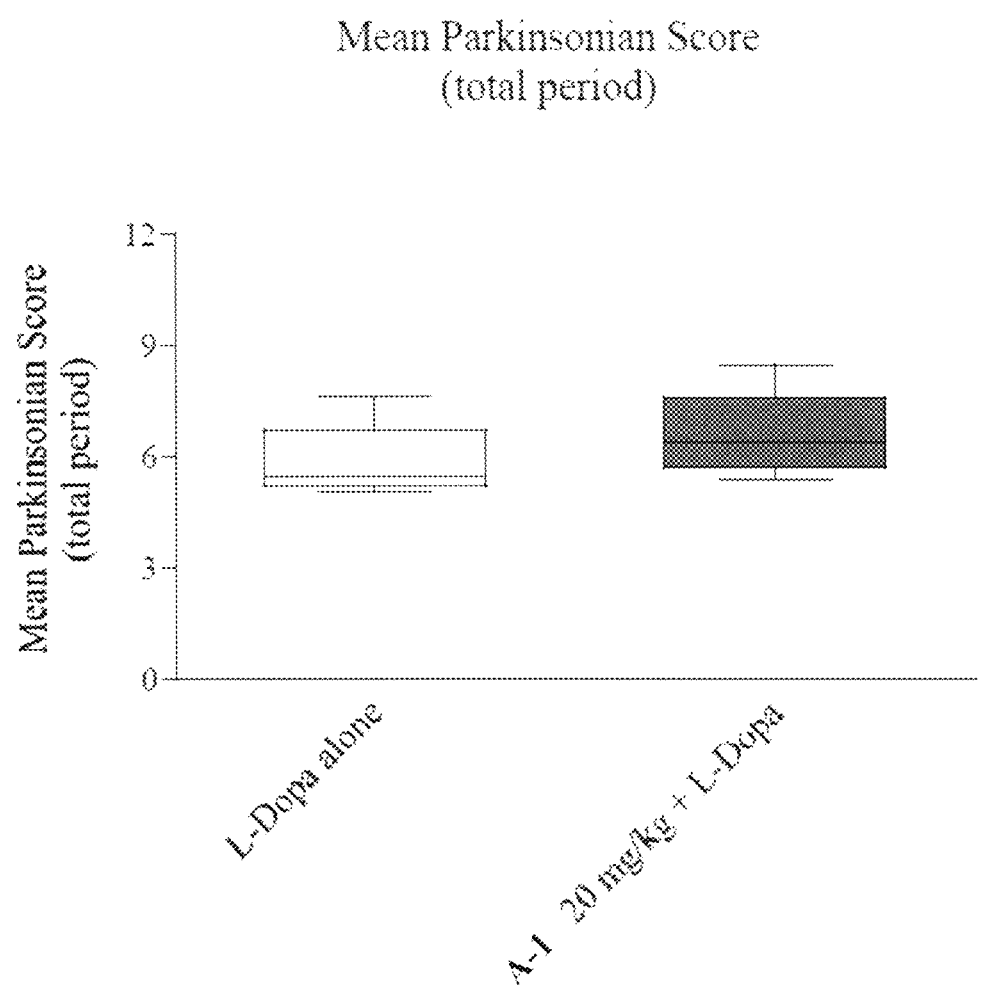
FIG. 2 provides a bar chart showing mean Parkinsonian Score (total period) after L-dopa administration in parkinsonian primates.
Figure 3:
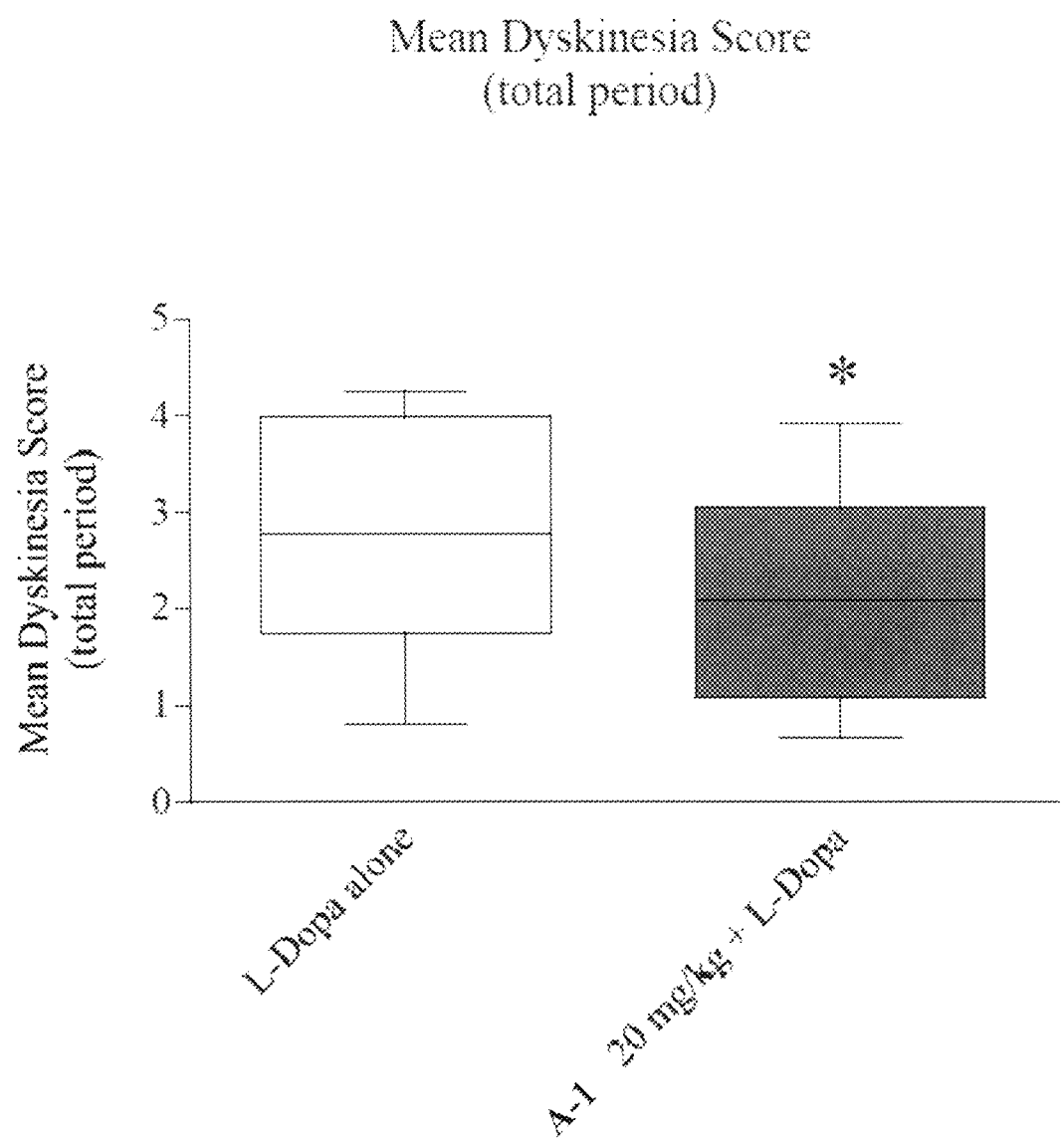
FIG. 3 provides a bar chart showing mean Dyskinesia Score (total period) after L-dopa administration in parkinsonian primates.
Figure 4:
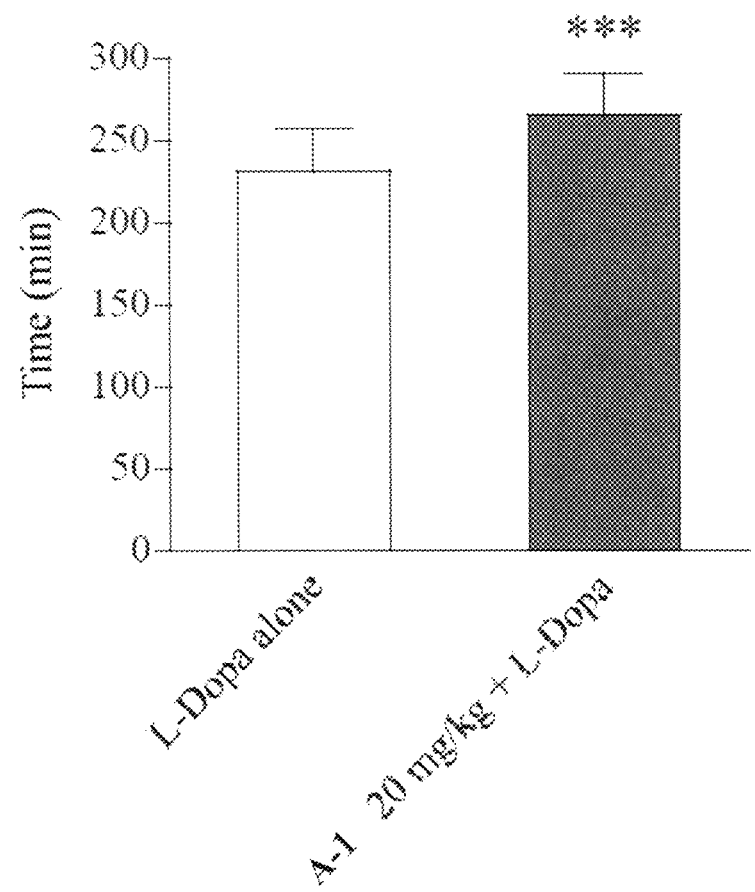
FIG. 4 provides a bar chart showing duration of L-dopa response after L-dopa administration in parkinsonian primates.

The drawings are intended to depict only typical aspects of the disclosure, and therefore should not be considered as limiting the scope of the disclosure.

DETAILED DESCRIPTION OF INVENTION

Nicotinic Acetylcholine Receptor Alpha 7 Agonist:

As used herein a "α7-nAChR agonist" is a compound that binds to a receptor comprising a α7-nAChR subunit in vivo and in vitro and is activating the receptor to perform its physiological function. Activation can be measured by the method disclosed in WO2001/85727, i.e. a functional affinity assay at the homomeric alpha 7 nicotinic acetylcholine receptor (α7 nAChR) carried out with a rat pituitary cell line stably expressing the α7 nAChR. As read out, the calcium influx upon stimulation of the receptor compared to epibatidine is used. "α7-nAChR agonists" according to the invention typically induce calcium influx of at least 50% of the maximal influx evoked by epibatidine with an $EC_{50}$ value of at least 1 μM; preferred agonists induce calcium influx of at least 75% of the maximal influx evoked by epibatidine with an $EC_{50}$ value of at least 400 nM; more preferred agonists induce calcium influx of at least 85% of the maximal influx evoked by epibatidine with an $EC_{50}$ value of at least 50 nM.

In particular, preferred α7-nAChR agonists should be well absorbed from the gastrointestinal tract, should be sufficiently metabolically stable and possess favorable pharmacokinetic properties. Further preferred α7-nAChR agonists bind in-vivo potently to α7-nAChRs whilst showing little affinity for other receptors, especially for other nAChRs, e.g. α4β2 nAChR, for muscarinic acetylcholine receptors, e.g. M1, and/or the 5-HT$_3$ receptor. Further preferred α7-nAChR agonists cross the blood brain barrier effectively. Preferred α7-nAChR agonists should be non-toxic and demonstrate few side-effects. Furthermore, a preferred α7-nAChR agonist will be able to exist in a physical form that is stable, non-hygroscopic and easily formulated.

In one embodiment, the α7-nAChR agonist is selective for a receptor comprising a α7-nAChR subunit, since such an agonist would be expected to cause fewer side effects than a non-selective agonist to a treated subject. An agonist being selective for a receptor comprising a α7-nAChR subunit has a functional affinity to such a receptor to a much higher degree, e.g. at least 10-fold affinity difference in $EC_{50}$ value, preferably at least 20-fold, more preferably at least 50-fold, compared to any other nicotinic acetylcholine receptor. To assess the affinity of the α7-nAChR agonists of the invention on other nicotinic acetylcholine receptors, the method disclosed in WO2001/85727 can be used, i.e. to assess the affinity on human neuronal α4β2 nAChR, a similar functional assay is carried out using a human embryonic kidney cell line stable expressing the human α4β2 subtype and to assess the activity of the compounds of the invention on the "ganglionic subtype" and the "muscle type" of nicotinic receptor, similar functional assays are carried out with a human embryonic kidney cell line stably expressing the human "ganglionic subtype" or a cell line endogenously expressing the human "muscle type" of nicotinic receptors.

In the last 15 years much effort has been focused on developing selective α7 nAChR agonists leading to the discovery of many different chemotypes displaying said selective activity. These efforts are summarized the review from Horenstein et al (Mol Pharmacol, 2008, 74, 1496-1511, which describes no less than 9 different families of α7 nAChR agonists, in most of which selective agonists have been found. All compounds disclosed in FIG. 1 of said review are incorporated herein by reference. In fact, several drug candidates having an α7 nAChR agonist mode of action entered pre-clinical or even clinical testing (for review: Broad et al, Drugs of the Future, 2007, 32(2), 161-170; Romanelli et al, Expert Opin Ther Patents, 2007, 17(11), 1365-1377). Examples of such compounds—again belonging to a diversity of chemotypes—are MEM3454, MEM63908, SSR180711, GTS21, EVP6124, ABT107, ABT126, TC-5619, AZD-6319 and SAR-130479. Further α7 nAChR agonists and their use as pharmaceuticals are known, for example, from WO2001/85727, WO2004/022556, WO2005/118535, WO2005/123732, WO2006/005608, WO2007/045478, WO2007/068476 and WO2007/068475.

In one embodiment, the α7-nAChR agonist is a compound of formula (I)

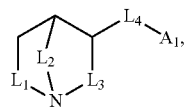

wherein
$L_1$ is —$CH_2$—; $L_2$ is —$CH_2$— or —$CH_2$—$CH_2$—; and $L_3$ is —$CH_2$— or —$CH(CH_3)$—; or
$L_1$ is —$CH_2$—$CH_2$—; $L_2$ is —$CH_2$—; and $L_3$ is —$CH_2$—$CH_2$—;

$L_4$ is a group selected from

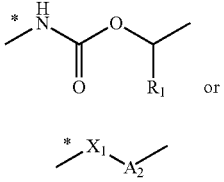
L4a or

*—X₁—A₂
L4b wherein the bond marked with the asterisk is attached to the azabicycloalkyl moiety;
$R_1$ is hydrogen or $C_{1-4}$alkyl;
$X_1$ is —O— or —NH—;
$A_2$ is selected from

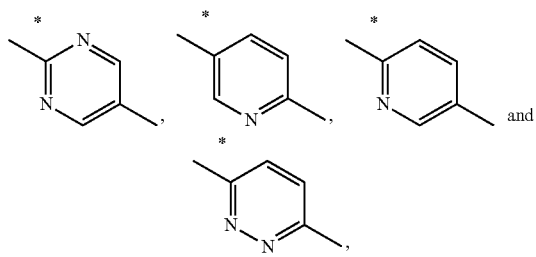

wherein the bond marked with the asterisk is attached to $X_1$;
$A_1$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen;
each $R_2$ independently is $C_{1-6}$alkyl, $C_{1-6}$halogenalkyl, $C_{1-6}$alkoxy, $C_{1-6}$halogenalkoxy, halogen, cyano or a three- to six-membered monocyclic ring system which may be aromatic, saturated or partially saturated and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;
or two $R_2$ at adjacent ring atoms form a $C_{3-4}$alkylene group, wherein 1-2 carbon atoms may be replaced by $X_2$, and wherein the $C_{3-4}$alkylene group may be substituted once or more than once by $R_3$;
each $X_2$ independently is —O— or —N($R_4$)—;
each $R_4$ independently is hydrogen or $C_{1-6}$alkyl; and
each $R_3$ independently is halogen or $C_{1-6}$alkyl;
in free base form or in acid addition salt form.

In one embodiment, the α7-nAChR agonist is a compound of formula (II)

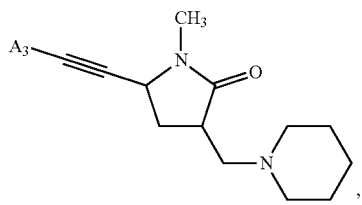

(II)

wherein
$A_3$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_5$, and wherein a substituent on a nitrogen in a heterocyclic ring system may not be halogen;
each $R_5$ independently is $C_{1-6}$alkyl, $C_{1-6}$halogenalkyl, $C_{1-6}$alkoxy, $C_{1-6}$halogenalkoxy, halogen, cyano, amino or a three- to six-membered monocyclic ring system which may be aromatic, saturated or partially saturated and which may contain from 1 to 4 hetero atoms selected from nitrogen, oxygen and sulfur, and wherein each ring system may contain not more than 2 oxygen atoms and not more than 2 sulfur atoms, and wherein each ring system may in turn be substituted once or more than once by $C_{1-6}$alkyl, $C_{1-6}$halogenalkyl, $C_{1-6}$alkoxy, $C_{1-6}$halogenalkoxy, halogen or cyano, and wherein a substituent on a nitrogen in a heterocyclic ring system may not be halogen;
or two $R_5$ at adjacent ring atoms form a $C_{3-4}$alkylene group, wherein 1-2 carbon atoms may be replaced by $X_3$, and wherein the $C_{3-4}$alkylene group may be substituted once or more than once by $R_6$;
each $X_3$ independently is —O— or —N($R_7$)—;
each $R_7$ independently is hydrogen or $C_{1-6}$alkyl; and
each $R_6$ independently is halogen or $C_{1-6}$alkyl;
in free base form or in acid addition salt form.

Unless indicated otherwise, the expressions used in this invention have the following meaning:
"Alkyl" represents a straight-chain or branched-chain alkyl group, for example, methyl, ethyl, n- or iso-propyl, n-, iso-, sec- or tert-butyl, n-pentyl, n-hexyl; $C_{1-6}$alkyl preferably represents a straight-chain or branched-chain $C_{1-4}$alkyl with particular preference given to methyl, ethyl, n-propyl, iso-propyl and tert-butyl.

Each alkyl part of "alkoxy", "halogenalkyl" and so on shall have the same meaning as described in the above-mentioned definition of "alkyl", especially regarding linearity and preferential size.

A substituent being substituted "once or more than once", for example as defined for $A_1$, is preferably substituted by one to three substituents.

Halogen is generally fluorine, chlorine, bromine or iodine; preferably fluorine, chlorine or bromine. Halogenalkyl groups preferably have a chain length of 1 to 4 carbon atoms and are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3,3,3-pentafluoropropyl or 2,2,3,4,4,4-hexafluorobutyl; preferably —$CF_3$, —$CHF_2$, —$CH_2F$, —CHF—$CH_3$, —$CF_2CH_3$, or —$CH_2CF_3$.

In the context of the invention, the definitions of "two $R_2$ at adjacent ring atoms form a $C_{3-4}$alkylene group, wherein 1-2 carbon atoms may be replaced by $X_2$" or "two $R_5$ at adjacent ring atoms form a $C_{3-4}$alkylene group, wherein 1-2 carbon atoms may be replaced by $X_3$" encompass —$CH_2$—$CH_2$—$CH_2$—, —$CH_2$—$CH_2$—$CH_2$—$CH_2$—, —O—$CH_2$—O—, —O—$CH_2$—$CH_2$—O— and —$CH_2$—$CH_2$—NH—. An example of a substituted group is —$CH_2$—$CH_2$—N($CH_3$)—.

In the context of the invention, the definition of $A_1$ or $A_3$ as a "five- to ten-membered monocyclic or fused polycyclic aromatic ring system" encompasses a $C_6$— or $C_{10}$-aromatic hydrocarbon group or a five- to ten-membered heterocyclic aromatic ring system. "Polycyclic" means preferably bicyclic.

In the context of the invention, the definition of $R_2$ as a "three- to six-membered monocyclic ring system" encompasses a $C_6$-aromatic hydrocarbon group, a five- to six-membered heterocyclic aromatic ring system and a three- to six-membered monocyclic aliphatic or heterocyclic ring system.

A $C_6$— or $C_{10}$-aromatic hydrocarbon group is typically phenyl or naphthyl, especially phenyl.

Preferably, but also depending on substituent definition, "five- to ten-membered heterocyclic aromatic ring systems" consist of 5 to 10 ring atoms of which 1-3 ring atoms are hetero atoms. Such heterocyclic aromatic ring systems may be present as a single ring system or as bicyclic or tricyclic ring systems; preferably as single ring systems or as benz-annelated ring systems. Bicyclic or tricyclic ring systems may be formed by annelation of two or more rings, or by a bridging atom, e.g. oxygen, sulfur, nitrogen. Examples of heterocyclic ring systems are: imidazo[2,1-b]thiazole, pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, isothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pteridine, and the corresponding benz-annelated heterocycles, e.g. indole, isoindole, coumarin, isoquinoline, quinoline and the like. Preferred heterocycles are: imidazo[2,1-b]thiazole, oxazole, isoxazole, thiazole, isothiazole, triazole, pyrrole, furane, tetrahydrofurane, pyridine, pyrimidine, imidazole or pyrazole.

In the context of the invention, three- to six-membered monocyclic aliphatic ring systems are typically cyclopropyl, cyclobutyl, cyclopentyl or cyclohexyl.

On account of asymmetrical carbon atom(s) that may be present in the compounds of formula (I) and compounds of formula (II), the compounds may exist in optically active form or in form of mixtures of optical isomers, e.g. in form of racemic mixtures or diastereomeric mixtures. All optical isomers and their mixtures, including racemic mixtures, are part of the present invention.

In one embodiment, the α7-nAChR agonist is a compound of formula (I)

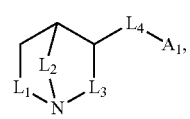

wherein $L_1$ is —$CH_2$—; $L_2$ is —$CH_2$—$CH_2$—; and $L_3$ is —$CH_2$— or —$CH(CH_3)$—;

$L_4$ is a group selected from

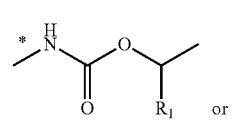

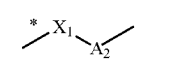

wherein the bond marked with the asterisk is attached to the azabicycloalkyl moiety;

$R_1$ is hydrogen or $C_{1-4}$alkyl;

$X_1$ is —O— or —NH—;

$A_2$ is selected from

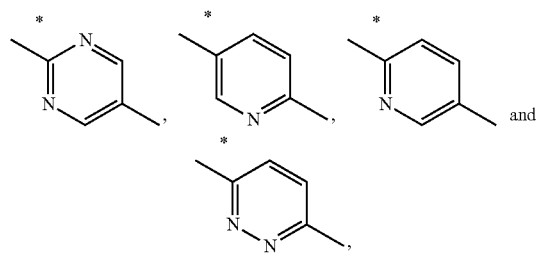

wherein the bond marked with the asterisk is attached to $X_1$;

$A_1$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen; and each $R_2$ independently is $C_{1-6}$alkyl, $C_{1-6}$halogenalkyl, $C_{1-6}$alkoxy, $C_{1-6}$halogenalkoxy or halogen.

In one embodiment, the α7-nAChR agonist is a compound of formula (I)

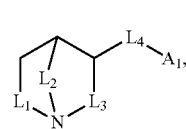

wherein
$L_1$ is —$CH_2$—; $L_2$ is —$CH_2$—$CH_2$—; and $L_3$ is —$CH_2$—;
$L_4$ is

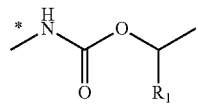

L4a wherein the bond marked with the asterisk is attached to the azabicycloalkyl moiety;
$R_1$ is hydrogen or $C_{1-4}$alkyl;
$A_1$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen; and
each $R_2$ independently is $C_{1-6}$alkyl, $C_{1-6}$halogenalkyl, $C_{1-6}$alkoxy, $C_{1-6}$halogenalkoxy or halogen.

In one embodiment, the α7-nAChR agonist is a compound of formula (I)

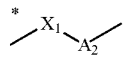

(I)

wherein
$L_1$ is —$CH_2$—; $L_2$ is —$CH_2$—$CH_2$—; and $L_3$ is —$CH_2$— or —$CH(CH_3)$—;
$L_4$ is

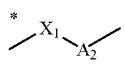

L4b wherein the bond marked with the asterisk is attached to the azabicycloalkyl moiety;
$X_1$ is —O— or —NH—;
$A_2$ is selected from

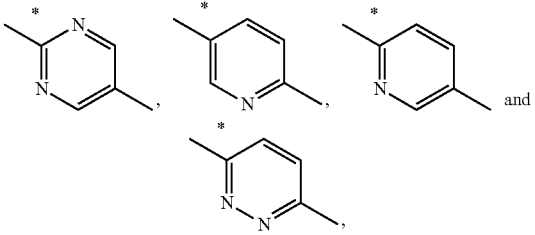

wherein the bond marked with the asterisk is attached to $X_1$;
$A_1$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen; and
each $R_2$ independently is $C_{1-6}$alkyl, $C_{1-6}$halogenalkyl, $C_{1-6}$alkoxy, $C_{1-6}$halogenalkoxy or halogen.

In one embodiment, the α7-nAChR agonist is a compound of formula (I)

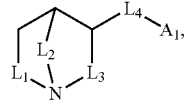

(I)

wherein
$L_1$ is —$CH_2$—$CH_2$—; $L_2$ is —$CH_2$—; and $L_3$ is —$CH_2$—$CH_2$—;
$L_4$ is L4b wherein the bond marked with the asterisk is attached to the azabicycloalkyl moiety;
$X_1$ is —O— or —NH—;
$A_2$ is selected from wherein the bond marked with the asterisk is attached to $X_1$;
$A_1$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by $R_2$, and wherein a substituent on a nitrogen in a heterocyclic ring system may not be halogen; and
each $R_2$ independently is $C_{1-6}$alkyl, $C_{1-6}$halogenalkyl, $C_{1-6}$alkoxy, $C_{1-6}$halogenalkoxy or halogen.

In one embodiment, the α7-nAChR agonist is a compound of formula (II)

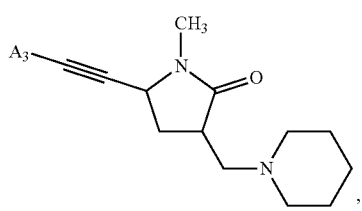

(II)

wherein

A$_3$ is a five- to ten-membered monocyclic or fused polycyclic aromatic ring system which may contain from 1 to 4 hetero atoms selected from nitrogen, oxygen and sulfur, wherein the ring system may contain not more than 2 oxygen atoms and not more than 2 sulfur atoms, and wherein the ring system may be substituted once or more than once by R$_5$, and wherein a substituent on a nitrogen in a heterocyclic ring system may not be halogen; and each R$_5$ independently is C$_{1-6}$alkyl, C$_{1-6}$halogenalkyl, C$_{1-6}$alkoxy, C$_{1-6}$halogenalkoxy, amino or halogen.

In one embodiment, the α7-nAChR agonist is a compound selected from Group P1;

Group P1 is the group consisting of

A-1: (S)-(1-aza-bicyclo[2.2.2]oct-3-yl)-carbamic acid (S)-1-(2-fluoro-phenyl)-ethyl ester;

A-2: (R)-(1-aza-bicyclo[2.2.2]oct-3-yl)-carbamic acid (R)-1-(2-chloro-phenyl)-ethyl ester;

A-3: (S)-(1-aza-bicyclo[2.2.2]oct-3-yl)-carbamic acid (S)-1-phenyl-ethyl ester;

B-1: (R)-3-(5-phenyl-pyrimidin-2-yloxy)-1-aza-bicyclo[2.2.2]octane;

B-2: (R)-3-(5-p-tolyl-pyrimidin-2-yloxy)-1-aza-bicyclo[2.2.2]octane;

B-3: (R)-3-(5-(2-fluoro-4-methyl-phenyl)-pyrimidin-2-yloxy)-1-aza-bicyclo[2.2.2]octane;

B-4: (R)-3-(5-(3,4-dimethyl-phenyl)-pyrimidin-2-yloxy)-1-aza-bicyclo[2.2.2]octane;

B-5: (R)-3-(6-p-tolyl-pyridin-3-yloxy)-1-aza-bicyclo[2.2.2]octane;

B-6: (R)-3-(6-phenyl-pyridin-3-yloxy)-1-aza-bicyclo[2.2.2]octane;

B-7: (R)-3-(6-(3,4-dimethyl-phenyl)-pyridin-3-yloxy)-1-aza-bicyclo[2.2.2]octane;

B-8: (R)-3-[6-(2-fluoro-4-methyl-phenyl)-pyridazin-3-yloxy]-1-aza-bicyclo[2.2.2]octane;

B-9: (R)-3-[6-(4,5-dimethyl-2-fluoro-phenyl)-pyridazin-3-yloxy]-1-aza-bicyclo[2.2.2]octane;

B-10: (R)-3-[6-(3,4-dimethyl-phenyl)-pyridazin-3-yloxy]-1-aza-bicyclo[2.2.2]octane;

B-11: (R)-3-[6-(4-methyl-phenyl)-pyridazin-3-yloxy]-1-aza-bicyclo[2.2.2]octane;

B-12: (R)-3-[6-(2,5-difluoro-4-methyl-phenyl)-pyridazin-3-yloxy]-1-aza-bicyclo[2.2.2]octane;

B-13: (2S,3R)-3-[6-(1H-indol-5-yl)-pyridazin-3-yloxy]-2-methyl-1-aza-bicyclo[2.2.2]octane;

B-14: (2R,3S)-3-[6-(1H-indol-5-yl)-pyridazin-3-yloxy]-2-methyl-1-aza-bicyclo[2.2.2]octane;

B-15: (2S,3R)-3-[5-(1H-indol-5-yl)-pyrimidin-2-yloxy]-2-methyl-1-aza-bicyclo[2.2.2]octane;

B-16: (2R,3S)-3-[5-(1H-indol-5-yl)-pyrimidin-2-yloxy]-2-methyl-1-aza-bicyclo[2.2.2]octane;

B-17: 3-[6-(1H-indol-5-yl)-pyridin-3-yloxy]-2-methyl-1-aza-bicyclo[2.2.2]octane;

B-18: (2S,3R)-2-methyl-3-[6-(5-methyl-thiophen-2-yl)-pyridazin-3-yloxy]-1-aza-bicyclo[2.2.2]octane;

B-19: 3-[6-(2,3-dimethyl-1H-indol-5-yl)-pyridazin-3-yloxy]-2-methyl-1-aza-bicyclo[2.2.2]octane;

B-20: trans-2-methyl-1-aza-bicyclo[2.2.2]oct-3-yl)-(6-phenyl-pyridin-3-yl)-amine;

B-21: trans-[6-(1H-indol-5-yl)-pyridin-3-yl]-(2-methyl-1-aza-bicyclo[2.2.2]oct-3-yl)-amine;

C-1: (4S,5R)-4-[5-(1H-indol-5-yl)-pyrimidin-2-yloxy]-1-aza-bicyclo[3.3.1]nonane;

C-2: 5-{2-[(4S,5R)-(1-aza-bicyclo[3.3.1]non-4-yl)oxy]-pyrimidin-5-yl}-1,3-dihydro-indol-2-one;

C-3: (4S,5R)-4-[6-(1H-indol-5-yl)-pyridin-3-yloxy]-1-aza-bicyclo[3.3.1]nonane;

C-4: (4S,5R)-4-[5-(1H-indol-5-yl)-pyridin-2-yloxy]-1-aza-bicyclo[3.3.1]nonane;

C-5: (4S,5R)-4-[6-(1H-indol-5-yl)-pyridazin-3-yloxy]-1-aza-bicyclo[3.3.1]nonane;

C-6: 5-{6-[(4S,5R)-(1-aza-bicyclo[3.3.1]non-4-yl)oxy]-pyridazin-3-yl}-1,3-dihydro-indol-2-one;

C-7: (1-aza-bicyclo[3.3.1]non-4-yl)-[5-(1H-indol-5-yl)-pyridin-2-yl]-amine;

C-8: (1-aza-bicyclo[3.3.1]non-4-yl)-[5-(1H-indol-5-yl)-pyrimidin-2-yl]-amine;

C-9: (1-aza-bicyclo[3.3.1]non-4-yl)-[6-(1H-indol-5-yl)-pyridin-3-yl]-amine;

C-10: (1-aza-bicyclo[3.3.1]non-4-yl)-[6-(1H-indol-5-yl)-pyridin-3-yl]-amine;

C-11: (1-aza-bicyclo[3.3.1]non-4-yl)-[5-(1H-indol-4-yl)-pyrimidin-2-yl]-amine;

C-12: (1-aza-bicyclo[3.3.1]non-4-yl)-[6-(1H-indol-5-yl)-pyridazin-3-yl]-amine;

D-1: 5-benzofuran-5-ylethynyl-1-methyl-3-piperidin-1-ylmethyl-pyrrolidin-2-one;

D-2: 1-methyl-5-phenylethynyl-3-piperidin-1-ylmethyl-pyrrolidin-2-one;

D-3: 1-methyl-5-(1-methyl-1H-indol-5-ylethynyl)-3-piperidin-1-ylmethyl-pyrrolidin-2-one;

D-4: 5-(3-Amino-phenylethynyl)-1-methyl-3-piperidin-1-ylmethyl-pyrrolidin-2-one;

E-1: 4-(5-phenyl-1,3,4-thiadiazol-2-yloxy)-1 azatricyclo[3.3.1.1$^{3,7}$]decane having the formula

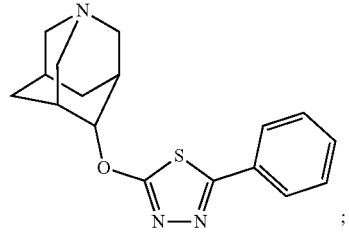 [SMILES: c1ccc(-c2nnc(OC3C4CC5CC3CN(C5)C4)s2)cc1]

E-1a: (4S)-4-(5-phenyl-1,3,4-thiadiazol-2-yloxy)-1 azatricyclo[3.3.1.1$^{3,7}$]decane;

E-1b: 4-(6-(1H-indol-5-yl)-pyridazin-3-yloxy)-1 azatricyclo[3.3.1.1$^{3,7}$]decane;

E-1c: 4-(6-(1H-indol-5-yl)-pyridin-3-yloxy)-1 azatricyclo[3.3.1.1$^{3,7}$]decane;

E-1d: 4-(5-(1H-indol-5-yl)-pyrimidin-2-yloxy)-1 azatricyclo[3.3.1.1$^{3,7}$]decane;

E-2: 2-(6-phenylpyridazine-3-yl)octahydropyrrolo[3,4-c]pyrrole having the formula

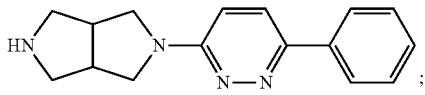

E-3: 5-[6-(5-methyl-hexahydro-pyrrolo[3,4-c]pyrrol-2-yl-pyridazin-3-yl]1H-indole having the formula

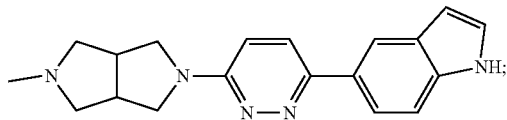 [SMILES: CN1CC2CN(c3ccc(-c4ccc5[nH]ccc5c4)nn3)CC2C1]

E-3a: 5-[6-(cis-5-methyl-hexahydro-pyrrolo[3,4-c]pyrrol-2-yl-pyridazin-3-yl]1H-indole;
E-4: 5-[5-{6-methyl-3,6-diaza-bicyclo[3.2.0]hept-3-yl}-pyridin-2-yl]-1H-indole having the formula

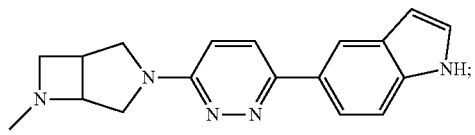 [SMILES: CN1CC2CN(c3ccc(-c4ccc5[nH]ccc5c4)nn3)CC21]

E-4a: 5-[5-{(1R,5R)-6-methyl-3,6-diaza-bicyclo[3.2.0]hept-3-yl}-pyridin-2-yl]-1H-indole
E-5: 2-Methyl-5-(6-phenyl-pyridazin-3-yl)-octahydro-pyrrolo[3,4-c]pyrrole having the formula

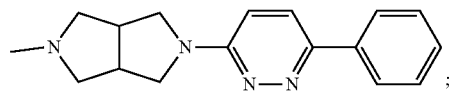 [SMILES: CN1CC2CN(c3ccc(-c4ccccc4)nn3)CC2C1]

E-6: 5-{6-[1-azabicyclo[2.2.2]oct-3-yloxy]pyridazin-3-yl}-1H-indole;
E-6a: 5-{6-[(3R)-1-azabicyclo[2.2.2]oct-3-yloxy]pyridazin-3-yl}-1H-indole;
E-7: 5-{6-[1-azabicyclo[2.2.2]oct-3-yloxy]pyridazin-3-yl}-1,3-dihydro-indol-2-one;
E-7a: 5-{6-[(3R)1-azabicyclo[2.2.2]oct-3-yloxy]pyridazin-3-yl}-1,3-dihydro-indol-2-one;
E-8: N-(1-azabicyclo[2.2.2]oct-3-yl)-1H-indazole-3-carboxamide;
E-8a: N-((3R)-1-azabicyclo[2.2.2]oct-3-yl)-1H-indazole-3-carboxamide
E-8b: N-((3S)-1-azabicyclo[2.2.2]oct-3-yl)-1H-indazole-3-carboxamide
E-9: N-(1-azabicyclo[2.2.2]oct-3-yl)-5-(trifluoromethoxy)-1H-indazole-3-carboxamide;
E-9a: N-((3R)-1-azabicyclo[2.2.2]oct-3-yl)-5-(trifluoromethoxy)-1H-indazole-3-carboxamide;
E-9b: N-((3S)-1-azabicyclo[2.2.2]oct-3-yl)-5-(trifluoromethoxy)-1H-indazole-3-carboxamide;
E-10: N-(2-((3-pyridinyl)methyl)-1-azabicyclo[2.2.2]oct-3-yl)benzofuran-2-carboxamide;
E-10a: (2S,3R)—N-(2-((3-pyridinyl)methyl)-1-azabicyclo[2.2.2]oct-3-yl)benzofuran-2-carboxamide;
E-11: N-(2-((3-pyridinyl)methyl)-1-azabicyclo[2.2.2]oct-3-yl)-3,5-difluorobenzamide;
E-11a: (2S,3R)—N-(2-((3-pyridinyl)methyl)-1-azabicyclo[2.2.2]oct-3-yl)-3,5-difluorobenzamide;
E-11 b: N-(2-((3-pyridinyl)methyl)-1-azabicyclo[2.2.2]oct-3-yl)-5-methylthiophene-2-carboxamide;
E-11c: (2S,3R)—N-(2-((3-pyridinyl)methyl)-1-azabicyclo[2.2.2]oct-3-yl)-5-methylthiophene-2-carboxamide;
E-11 d: N-(2-((3-pyridinyl)methyl)-1-azabicyclo[2.2.2]oct-3-yl)-5-(2-pyridinyl)thiophene-2-carboxamide;

E-11e: (2S,3R)—N-(2-((3-pyridinyl)methyl)-1-azabicyclo[2.2.2]oct-3-yl)-5-(2-pyridinyl)thiophene-2-carboxamide;
E-12: 4-(5-methyloxazolo[4,5-b]pyridin-2-yl)-1,4-diazabicyclo[3.2.2]nonane;
E-13: [N-[(3R)-1-azabicyclo[2.2.2]oct-3-yl]-4-chlorobenzamide;
E-14: furo[2,3-c]pyridine-5-carboxylic acid (1-aza-bicyclo[2.2.2]oct-3-yl)-amide;
E-15: 2,3-dihydro-benzo[1,4]dioxine-6-carboxylic acid (1-aza-bicyclo[2.2.2]oct-3-yl)-amide;
E-16: 5-morpholin-4-yl-pentanoic acid (4-pyridin-3-yl-phenyl)-amide;
E-17: N-{4-[4-(2,4-dimethoxy-phenyl)-piperazin-1-yl]-butyl}-4-pyridin-2-yl-benzamide;
E-18: 1-[6-(4-fluorophenyl)pyridin-3-yl]-3-(4-piperidin-1-ylbutyl)-urea;
E-19: 7,8,9,10-tetrahydro-6,10-methano-6H-pyrazino-(2,3-h)(3)-benzazepine;
E-20: (2'R)-spiro-[1-azabicyclo[2.2.2]octane-3,2'(3'H)-furo[2,3-b]pyridine];
E-21: 1,4-Diaza-bicyclo[3.2.2]nonane-4-carboxylic acid 4-bromo-phenyl ester;
E-22: 3-[1-(2,4-Dimethoxy-phenyl)-meth-(E)-ylidene]-3,4,5,6-tetrahydro-[2,3']bipyridinyl;
E-23: 7-(2-Methoxy-phenyl)-benzofuran-2-carboxylic acid (1-aza-bicyclo[2.2.2]oct-3-yl)-amide;
E-24: N-methyl-1-{5-[3'H-spiro[4-azabicyclo[2.2.2]octane-2,2'-furo[2,3-b]pyridin]-5'-yl]-2-thienyl}methanamine having the formula

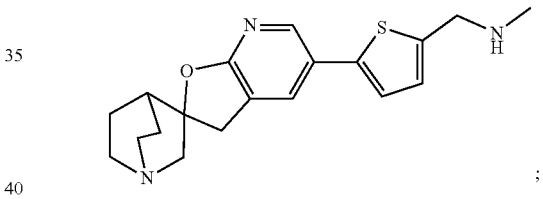

E-24a: N-methyl-1-{5-[(2R)-3'H-spiro[4-azabicyclo[2.2.2]octane-2,2'-furo[2,3-b]pyridin]-5'-yl]-2-thienyl}methanamine;
E-24b: N-methyl-1-{5-[(2S)-3'H-spiro[4-azabicyclo[2.2.2]octane-2,2'-furo[2,3-b]pyridin]-5'-yl]-2-thienyl}methanamine;
E-25a: 6-[(Anilinocarbonyl)amino]-N-[(3R)-1-azabicyclo[2.2.2]oct-3-yl]-1-benzothiophene-2-carboxamide;
E-25b: N-[(3R)-1-Azabicyclo[2.2.2]oct-3-yl]-6-({[(4-chlorophenyl)amino]carbonyl}amino)-1-benzothiophene-2-carboxamide;
E-25c: N-[(3R)-1-Azabicyclo[2.2.2]oct-3-yl]-6-({[(2-methoxyphenyl)amino]carbonyl}-amino)-1-benzothiophene-2-carboxamide;
E-25d: N-[(3R)-1-Azabicyclo[2.2.2]oct-3-yl]-6-({[(4-methoxyphenyl)amino]carbonyl}-amino)-1-benzothiophene-2-carboxamide;
E-25e: N-[(3R)-1-Azabicyclo[2.2.2]oct-3-yl]-6-({[(2-phenylethyl)amino]carbonyl}amino)-1-benzothiophene-2-carboxamide;
E-25f: N-[(3R)-1-Azabicyclo[2.2.2]oct-3-yl]-6-({[(3-cyanophenyl)amino]carbonyl}amino)-1-benziophene-2-carboxamide;
E-25g: N-[(3R)-1-Azabicyclo[2.2.2]oct-3-yl]-6-({[(3-bromophenyl)amino]carbonyl}amino)-1-benzothiophene-2-carboxamide;

E-25h: N-[(3R)-1-Azabicyclo[2.2.2]oct-3-yl]-6-({[(2-elhoxyphenyl)amino]carbonyl)amino)-1-benzothiophene-2-carboxamide;

E-25i: N-[(3R)-1-Azbicyclo[2.2.2]oct-3-yl]-6-({[(4-(dimethylamino)phenyl)amino]-carbonyl)amino)-1-benzothiophene-2-carboxamide;

E-25j: N-(3R)-1-Azabicyclo[2.2.2]oct-3-yl]-6-({[(2-nitrophenyl)amino]carbonyl}amino)-1-benzothiophene-2-carboxamide;

E-25k: N-[(3R)-1-Azabicyclo[2.2.2]oct-3-yl]-6-({[(2,6-difluorophenyl)amino]carbonyl}-amino)-1-benzothiophene-2-carboxamide;

E-25l: N-[(3R)-1-Azabicyclo[2.2.2]oct-3-yl]-6-({[(2,4-dichlorophenyl)amino]carbonyl}-amino)-1-benzothiophene-2-carboxamide;

E-25m: N-[(3R)-1-Azabicyclo[2.2.2]oct-3-yl]-6-[({[3-(trifluoromethyl)phenyl]amino]-carbonyl)amino]-1-benzothiophene-2-carboxamide;

E-25n: N-[(3R)-1-Azabicyclo[2.2.2]oct-3-yl]-6-({[(3,4,5-trimethoxyphenyl)amino]-carbonyl}amino)-1-benzothiophene-2-carboxamide;

E-25o: N-[(3R)-1-Azabicyclo[2.2.2]oct-3-yl]-6-[({[4-methoxy-3-(trifluoromethyl)phenyl]-amino}carbonyl)amino]-1-benzothiophene-2-carboxamide;

E-25p: N-{(3R)-1-Azabicyclo[2.2.2]oct-3-yl]-6-[({[3-methoxyphenyl]amino}carbonyl)-amino]-1-benzothiophene-2-carboxamide;

E-25q: N-[(3R)-1-Azabicyclo[2.2.2]oct-3-yl]-6-[({[3-trifluoromethoxyphenyl]amino}-carbonyl)-amino]-1-benzothiophene-2-carboxamide;

E-25r: N-[(3R)-1-Azabicyclo[2.2.2]oct-3-yl]-6-{[(tert-butylamino)carbonyl]amino}-1-benzothiophene-2-carboxamide;

E-25s: N-[(3R)-1-Azabicyclo[2.2.2]oct-3-yl]-6-{[(cyclohexylamino)carbonyl]amino}-1-benzothiophene-2-carboxamide;

E-25t: N-[(3R)-1-Azabicyclo[2.2.2]oct-3-yl]-6-[({[(1 S)-1-phenylethyl]amino}carbonyl-amino]-1-benzothiophene-2-carboxamide;

E-25u: 7-[(Anilinocarbonyl)amino]-N-[(3R)-1-azabicyclo[2.2.2]oct-3-yl]-1-benzothiophene-2-carboxamide;

E-25v: N-[(3R)-1-Azabicyclo[2.2.2]oct-3-yl]-6-({[(4-methoxyphenyl)amino]carbonyl}-amino)-1-benzofuran-2-carboxamide;

E-26a: N-[4-(2-Thienyl)phenyl]-1-azabicyclo[2.2.2]octane-3-carboxamide;

E-26b: N-[4'-(Hydroxymethyl)-1,1'-biphenyl-4-yl]-1-azabicyclo[2.2.2]octane-3-carboxamide;

E-26c: N-(4'-Fluoro-1,1'-biphenyl-4-yl)-1-azabicyclo[2.2.2]octane-3-carboxamide;

E-26d: N-(4'-Methylsulfanyl-1,1'-biphenyl-4-yl)-1-azabicyclo[2.2.2]octane-3-carboxamide;

E-26e: 2-(1-Azabicyclo[2.2.2]oct-3-yl)-N-(4'-fluoro-1,1'-biphenyl-4-yl)acetamide;

E-26f: 2-(1-Azabicyclo[2.2.2]oct-3-yl)-N-(4'-methoxy-1,1'-biphenyl-4-yl)acetamide;

E-26g: 2-(1-Azabicyclo[2.2.2]oct-3-yl)-N-(4'-fluoro-1,1'-biphenyl-3-yl)acetamide;

E-26h: 2-(1-Azabicyclo[2.2.2]oct-3-yl)-N-(3'-nitro-1,1'-biphenyl-4-yl)acetamide;

E-26i: 2-(1-Azabicyclo[2.2.2]oct-3-yl)-N-[4'-(hydroxymethyl)-1,1'-biphenyl-3-yl]acetamide;

E-26j: 2-(1-Azabicyclo[2.2.2]oct-3-yl)-N-[4'-(bromomethyl)-1,1'-biphenyl-4-yl]acetamide;

E-26k: 2-(1-Azabicyclo[2.2.2]oct-3-yl)-N-[2'-(hydroxymethyl)-1,1'-biphenyl-3-yl]acetamide;

E-26l: N-[3'(Acetylamino)-1,1'-biphenyl-4-yl]-2-(1-azabicyclo[2.2.2]oct-3-yl)acetamide;

E-26m: (3R)—N-[2'-(Hydroxymethyl)-1,1'-biphenyl-4-yl]-1-azabicyclo[2.2.2]octane-3-carboxamide;

E-26n: (3R)—N-[4'-(Hydroxymethyl)-1,1'-biphenyl-4-yl]-1-azabicyclo[2.2.2]octane-3-carboxamide;

E-26o: (3S)—N-[4'(Hydroxymethyl)-1,1'-biphenyl-4-yl]-1-azabicyclo[2.2.2]octane-3-carboxamide;

E-26p: (3R)—N-[4'-(4-Morpholinyl)-1,1'-biphenyl-4-yl]-1-azabicyclo[2.2.2]octane-3-carboxamide;

E-26q: (3R)—N-[4'-(Hydroxymethyl)-3'-(methoxy)-1,1'-biphenyl-4-yl]-1-azabicyclo[2.2.2]-octane-3-carboxamide;

E-26r: Methyl 4'-{[(3S)-1-azabicyclo[2.2.2]oct-3-ylcarbonyl]amino}-1,1'-biphenyl-4-carboxylate;

E-26s: 4'-{[(3S)-1-Azabicyclo[2.2.2]oct-3-ylcarbonyl]amino}-1,1'-biphenyl-4-carboxylic Acid;

E-26t: (3R)—N-[4'-(Hydroxy-1-methylethyl)-1,1'-biphenyl-4-yl]-1-azabicyclo[2.2.2]-octane-3-carboxamide;

E-26u: (3R)—N-[4'-(Aminocarbonyl)-1,1'-biphenyl-4-yl]-1-azabicyclo[2.2.2]octane-3-carboxamide;

E-26v: (3R)—N-[4'-(Hydroxymethyl)-3-fluoro-1,1'-biphenyl-4-yl]-1-azabicyclo[2.2.2]octane-3-carboxamide;

E-26w: (4'-{[(3R)-1-Azabicyclo[2.2.2]oct-3-ylcarbonyl]amino}-1,1'-biphenyl-4-yl)methyl Methylcarbamate;

E-26x: (4'-{[(3R)-1-Azabicyclo[2.2.2]oct-3-ylcarbonyl]amino}-1,1'-biphenyl-4-yl)methyl Isopropylcarbamate;

E-26y: (4'-{[(3R)-1-Azabicyclo[2.2.2]oct-3-ylcarbonyl]amino}-1,1'-biphenyl-4-yl)methyl Ethylcarbamate;

E-26z: the free base form of a compound being selected from Examples No 26, 27, 28, 29, 30, 31, 32, 33, 34 and 35 of WO2003/078431;

E-27a: 2-(1-Azabicyclo[2.2.2]oct-3-yl)-N-(7-bromo-1-benzothien-2-yl)acetamide;

E-27b: 2-(1-Azabicyclo[2.2.2]oct-3-yl)-N-(6-bromo-1-benzothien-2-yl)acetamide;

E-27c: 2-(1-Azabicyclo[2.2.2]oct-3-yl)-N-(7-quinolinyl)acetamide;

E-27d: 2-(1-Azabicyclo[2.2.2]oct-3-yl)-N-(2-naphthyl)acetamide;

E-27e: 2-(1-Azabicyclo[2.2.2]oct-3-yl)-N-(8-nitro-2-naphthyl)acetamide;

E-28a: N-(1-Azabicyclo[2.2.2]oct-3-yl)-6-quinolinecarboxamide;

E-28b: N-(1-Azabicyclo[2.2.2]oct-3-yl)-2-phenazinecarboxamide;

E-28c: N-(1-Azabicyclo[2.2.2]oct-3-yl)-7-quinolinecarboxamide;

E-28d: N-[(3R)-1-Azabicyclo[2.2.2]oct-3-yl]-6-quinolinecarboxamide;

E-28e: N-(1-Azabicyclo[2.2.2]oct-3-yl)-2-ethyl-7-quinolinecarboxamide;

E-28f: N-(1-Azabicyclo[2.2.2]oct-3-yl)-2-ethyl-6-quinolinecarboxamide;

E-28g: N-(1-Azabicyclo[2.2.2]oct-3-yl)-2-methyl-7-quinolinecarboxamide;

E-28h: N-(1-Azabicyclo[2.2.2]oct-3-yl)-2-methyl-6-quinolinecarboxamide;

E-28i: N-(1-Azabicyclo[2.2.2]oct-3-yl)-4-methyl-6-quinolinecarboxamide;

E-28j: N-(1-Azabicyclo[2.2.2]oct-3-yl)-2-propyl-6-quinolinecarboxamide;

E-28k: N-(1-Azabicyclo[2.2.2]oct-3-yl)-2-ethyl-4-methyl-6-quinolinecarboxamide;

E-28l: N-(1-Azabicyclo[2.2.2]oct-3-yl)-2-propyl-7-quinolinecarboxamide;

E-28m: N-(1-Azabicyclo[2.2.2]oct-3-yl)-2-ethyl-4-methyl-7-quinolinecarboxamide;

E-28n: N-(1-Azabicyclo[2.2.2]oct-3-yl)-4-(tetrahydro-2H-pyran-2-yl)-6-quinolinecarboxamide;

E-28o: N-(1-Azabicyclo[2.2.2]oct-3-yl)-4-(tetrahydro-2H-pyran-2-yl)-7-quinolinecarboxamide;

E-28p: N-(1-Azabicyclo[2.2.2]oct-3-yl)-2-phenyl-6-quinolinecarboxamide; and

E-28q: N-(1-Azabicyclo[2.2.2]oct-3-yl)-2-phenyl-7-quinolinecarboxamide;

wherein each of said compound is in free base form or in acid addition salt form.

In one embodiment, the α7-nAChR agonist is a compound selected from the group consisting of compound A-1, A-2 and A-3; wherein each of said compound is in free base form or in acid addition salt form.

In one embodiment, the α7-nAChR agonist is a compound selected from the group consisting of compound B-1, B-2, B-3, B-4, B-5, B-6, B-7, B-8, B-9, B-10, B-11, B-12, B-13, B-14, B-15, B-16, B-17, B-18, B-19, B-20 and B-21; wherein each of said compound is in free base form or in acid addition salt form.

In one embodiment, the α7-nAChR agonist is a compound selected from the group consisting of compound C-1, C-2, C-3, C-4, C-5, C-6, C-7, C-8, C-9, C-10, C-11 and C-12; wherein each of said compound is in free base form or in acid addition salt form.

In one embodiment, the α7-nAChR agonist is a compound selected from the group consisting of compound D-1, D-2, D-3 and D-4; wherein each of said compound is in free base form or in acid addition salt form.

In one embodiment, the α7-nAChR agonist is a compound selected from Group P2; Group P2 is the group consisting of compounds A-1, A-2, A-3, B-1, B-2, B-3, B-4, B-5, B-6, B-7, B-8, B-9, B-10, B-11, B-12, B-13, B-14, B-15, B-16, B-17, B-18, B-19, B-20, B-21, C-1, C-2, C-3, C-4, C-5, C-6, C-7, C-8, C-9, C-10, C-11, C-12, E-1, E-1a, E-1b, E-1c, E-1d, E-2, E-3, E-3a, E-4, E-4a, E-8, E-8a, E-8b, E-9, E-9a, E-9b, E-10, E-10a, E-11, E-11a, E-11b, E-11c, E-11d, E-11e, E-12, E-19, E-22, E-24, E-24a, E-24b, E-25a, E-25b, E-25c, E-25d, E-25e, E-25f, E-25g, E-25h, E-25i, E-25j, E-25k, E-25l, E-25m, E-25n, E-25o, E-25p, E-25q, E-25r, E-25s, E-25t, E-25u, E-25v, E-28a, E-28b, E-28c, E-28d, E-28e, E-28f, E-28g, E-28h, E-28i, E-28j, E-28k, E-28l, E-28m, E-28n, E-28o, E-28p and E-28q; wherein each of said compound is in free base form or in acid addition salt form.

In one embodiment, the α7-nAChR agonist is a compound selected from Group P3; Group P3 is the group consisting of compounds A-1, A-2, A-3, B-1, B-2, B-3, B-4, B-5, B-6, B-7, B-8, B-9, B-10, B-11, B-12, B-13, B-14, B-15, B-16, B-17, B-18, B-19, B-20, B-21, C-1, C-2, C-3, C-4, C-5, C-6, C-7, C-8, C-9, C-10, C-11, C-12, E-1, E-1a, E-1b, E-1c, E-1d, E-2, E-3, E-3a, E-4, E-4a, E-8, E-8a, E-8b, E-9, E-9a, E-9b, E-10, E-10a, E-11, E-11a, E-12, E-19, E-22, E-24, E-24a and E-24b; wherein each of said compound is in free base form or in acid addition salt form.

The compounds of formula (I) (e.g. compounds A-1 to A-3, B-1 to B-21 and C-1 to C-12) or compounds of formula (II) (e.g. compounds D-1 to D-4) and their manufacture are known from WO2001/85727, WO2004/022556, WO2005/118535, WO2005/123732, WO2006/005608, WO2007/045478, WO2007/068476 and WO2007/068475, or can be prepared analogously to said references.

Compounds E-1 and E-1a can be prepared according to WO2008/058096.

Compounds E-2, E-3, E-3a, E-4, E-4a and E-5 (A-582941) can be prepared according to WO2005/028477.

Compounds E-6, E-6a, E-7 and E7a can be prepared according to WO2006/065233 and/or WO2007/018738.

Compounds E-8, E-8a, E-8b, E-9, E-9a and E-9b can be prepared according to WO2004/029050 and/or WO2010/043515.

Compounds E-10 and E-10a can be prepared according to WO2004/076449 and/or WO2009/018505;

Compounds E-11, E-11a to E-11e can be prepared according to WO2004/076449 and/or WO2010/085724 and/or WO2010/056622;

Compounds E-12 (CP-810123) and Compound E-19 (varenicline) are described in O'Donnell et al, J Med Chem, 2010, 53, 1222-1237.

Compounds E-13 (PNU-282987), E-14 (PHA543613), E-21 (SSR-180771) and E-23 (ABBF) are described in Horenstein et al, Mol Pharmacol, 2008, 74, 1496-1511.

Compounds E-15 (PHA568487), E-16 (WAY-317538), E-17 (WAY-264620), E-20 (AZD-0328) and E-22 (GTS-21) are described in Haydar et al, Current Topics in Medicinal Chemistry, 2010, 10, 144-152.

Compound E-18 (WYE-103914) is described in Ghiron et al, J Med Chem, 2010, 53, 4379-4389.

Compound E-24, E-24a and E-24b are described in WO2007/133155 and/or WO2009/066107.

Compounds E-25a to E-25v are described in WO2004/013136.

Compounds E-26a to E-26z are described in WO2003/078431.

Compounds E-27a to E-27e are described in WO2003/078430.

Compounds E-28a to E-28q are described in WO2003/043991.

A further aspect of the invention concerns the use of a α7-nAChR agonist for the treatment (whether therapeutic or prophylactic), prevention or delay of progression of dyskinesia associated with dopamine agonist therapy in Parkinson's Disease; wherein said α7-nAChR agonist is a compound of formula (I).

A further aspect of the invention concerns the use of a α7-nAChR agonist for the treatment (whether therapeutic or prophylactic), prevention or delay of progression of dyskinesia associated with dopamine agonist therapy in Parkinson's Disease; wherein said α7-nAChR agonist is a compound selected from the Group P1.

A further aspect of the invention concerns the use of a α7-nAChR agonist for the treatment (whether therapeutic or prophylactic), prevention or delay of progression of dyskinesia associated with dopamine agonist therapy in Parkinson's Disease; wherein said α7-nAChR agonist is a compound selected from the Group P2.

A further aspect of the invention concerns the use of a α7-nAChR agonist for the treatment (whether therapeutic or prophylactic), prevention or delay of progression of dyskinesia associated with dopamine agonist therapy in Parkinson's Disease; wherein said α7-nAChR agonist is a compound selected from the Group P3.

A further aspect of the invention relates to a method for the treatment, prevention or delay of progression of dyskinesia associated with dopamine agonist therapy in Parkinson's Disease in a subject in need of such treatment, which comprises administering to said subject a therapeutically effective amount of a α7-nAChR agonist; wherein said α7-nAChR agonist is a compound of formula (I).

A further aspect of the invention relates to a method for the treatment, prevention or delay of progression of dyskinesia associated with dopamine agonist therapy in Parkinson's Disease in a subject in need of such treatment, which comprises administering to said subject a therapeutically effective amount of a α7-nAChR agonist; wherein said α7-nAChR agonist is a compound selected from the Group P1.

A further aspect of the invention relates to a method for the treatment, prevention or delay of progression of dyskinesia associated with dopamine agonist therapy in Parkinson's Disease in a subject in need of such treatment, which comprises administering to said subject a therapeutically effective amount of a α7-nAChR agonist; wherein said α7-nAChR agonist is a compound selected from the Group P2.

A further aspect of the invention relates to a method for the treatment, prevention or delay of progression of dyskinesia associated with dopamine agonist therapy in Parkinson's Disease in a subject in need of such treatment, which comprises administering to said subject a therapeutically effective amount of a α7-nAChR agonist; wherein said α7-nAChR agonist is a compound selected from the Group P3.

A further aspect of the invention relates to a method for the treatment, prevention or delay of progression of dyskinesia associated with dopamine agonist therapy in Parkinson's Disease in a subject in need of such treatment, which comprises (i) diagnosing dyskinesia associated with dopamine agonist therapy in Parkinson's Disease in said subject and (ii) administering to said subject a therapeutically effective amount of a α7-nAChR; wherein said α7-nAChR agonist is a compound of formula (I).

A further aspect of the invention relates to a method for the treatment, prevention or delay of progression of dyskinesia associated with dopamine agonist therapy in Parkinson's Disease in a subject in need of such treatment, which comprises (i) diagnosing dyskinesia associated with dopamine agonist therapy in Parkinson's Disease in said subject and (ii) administering to said subject a therapeutically effective amount of a α7-nAChR; wherein said α7-nAChR agonist is a compound selected from the Group P1.

A further aspect of the invention relates to a method for the treatment, prevention or delay of progression of dyskinesia associated with dopamine agonist therapy in Parkinson's Disease in a subject in need of such treatment, which comprises (i) diagnosing dyskinesia associated with dopamine agonist therapy in Parkinson's Disease in said subject and (ii) administering to said subject a therapeutically effective amount of a α7-nAChR; wherein said α7-nAChR agonist is a compound selected from the Group P2.

A further aspect of the invention relates to a method for the treatment, prevention or delay of progression of dyskinesia associated with dopamine agonist therapy in Parkinson's Disease in a subject in need of such treatment, which comprises (i) diagnosing dyskinesia associated with dopamine agonist therapy in Parkinson's Disease in said subject and (ii) administering to said subject a therapeutically effective amount of a α7-nAChR; wherein said α7-nAChR agonist is a compound selected from the Group P3.

A further aspect of the invention relates to a pharmaceutical composition comprising a α7-nAChR agonist for the treatment, prevention or delay of progression of dyskinesia associated with dopamine agonist therapy in Parkinson's Disease; wherein said α7-nAChR agonist is a compound of formula (I).

A further aspect of the invention relates to a pharmaceutical composition comprising a α7-nAChR agonist for the treatment, prevention or delay of progression of dyskinesia associated with dopamine agonist therapy in Parkinson's Disease; wherein said α7-nAChR agonist is a compound selected from the Group P1.

A further aspect of the invention relates to a pharmaceutical composition comprising a α7-nAChR agonist for the treatment, prevention or delay of progression of dyskinesia associated with dopamine agonist therapy in Parkinson's Disease; wherein said α7-nAChR agonist is a compound selected from the Group P2.

A further aspect of the invention relates to a pharmaceutical composition comprising a α7-nAChR agonist for the treatment, prevention or delay of progression of dyskinesia associated with dopamine agonist therapy in Parkinson's Disease; wherein said α7-nAChR agonist is a compound selected from the Group P3.

A further aspect of the invention relates to the use of a α7-nAChR agonist for the manufacture of a medicament for the treatment, prevention or delay of progression of dyskinesia associated with dopamine agonist therapy in Parkinson's Disease; wherein said α7-nAChR agonist is a compound of formula (I).

A further aspect of the invention relates to the use of a α7-nAChR agonist for the manufacture of a medicament for the treatment, prevention or delay of progression of dyskinesia associated with dopamine agonist therapy in Parkinson's Disease; wherein said α7-nAChR agonist is a compound selected from the Group P1.

A further aspect of the invention relates to the use of a α7-nAChR agonist for the manufacture of a medicament for the treatment, prevention or delay of progression of dyskinesia associated with dopamine agonist therapy in Parkinson's Disease; wherein said α7-nAChR agonist is a compound selected from the Group P2.

A further aspect of the invention relates to the use of a α7-nAChR agonist for the manufacture of a medicament for the treatment, prevention or delay of progression of dyskinesia associated with dopamine agonist therapy in Parkinson's Disease; wherein said α7-nAChR agonist is a compound selected from the Group P3.

Nicotinic Acetylcholine Receptor Alpha 7 Positive Allosteric Modulator:

As used herein a "α7-nAChR positive allosteric modulator" is a compound that binds to a receptor comprising a α7-nAChR subunit in vivo and in vitro and is potentiating the activation of the receptor when its physiological ligand (i.e. acetylcholine) is binding. Potentiation can be measured by the method disclosed in WO2001/85727, i.e. a functional affinity assay at the homomeric alpha 7 nicotinic acetylcholine receptor (α7 nAChR) carried out with a rat pituitary cell line stably expressing the α7 nAChR. As read out, the calcium influx upon stimulation of the receptor compared to acetylcholine-binding alone is used. "α7-nAChR positive allosteric modulators" according to the invention typically induce calcium influx of at least 200% of the maximal influx evoked by acetylcholine with an $EC_{50}$ value of at least 5000 nM; preferred agonists induce calcium influx of at least 300% of the maximal influx evoked by acetylcholine with an $EC_{50}$ value of at least 1000 nM; more preferred agonists induce calcium influx of at least 400% of the maximal influx evoked by epibatidine with an $EC_{50}$ value of at least 500 nM.

In particular, preferred α7-nAChR positive allosteric modulators should be well absorbed from the gastrointestinal tract, should be sufficiently metabolically stable and possess favorable pharmacokinetic properties.

Further preferred α7-nAChR positive allosteric modulators bind in-vivo potently to α7-nAChRs whilst showing little affinity for other receptors, especially for other nAChRs, e.g. α4β2 nAChR, for muscarinic acetylcholine receptors, e.g. M1, and/or the 5-HT$_3$ receptor. Further preferred α7-nAChR positive allosteric modulators cross the blood brain barrier effectively. Preferred α7-nAChR positive allosteric modulators should be non-toxic and demonstrate few side-effects. Furthermore, a preferred α7-nAChR positive allosteric modulator will be able to exist in a physical form that is stable, non-hygroscopic and easily formulated.

In one embodiment, the α7-nAChR positive allosteric modulator is selective for a receptor comprising a α7-nAChR subunit, since such a positive allosteric modulator would be expected to cause fewer side effects than a non-selective positive allosteric modulator to a treated subject. A positive allosteric modulator being selective for a receptor comprising a α7-nAChR subunit has a functional affinity to such a receptor to a much higher degree, e.g. at least 10-fold affinity difference in EC$_{50}$ value, preferably at least 20-fold, more preferably at least 50-fold, compared to any other nicotinic acetylcholine receptor. To assess the affinity of the α7-nAChR positive allosteric modulator of the invention on other nicotinic acetylcholine receptors, the method disclosed in WO2001/85727 can be used, i.e. to assess the affinity on human neuronal α4β2 nAChR, a similar functional assay is carried out using a human embryonic kidney cell line stable expressing the human α4β2 subtype and to assess the activity of the compounds of the invention on the "ganglionic subtype" and the "muscle type" of nicotinic receptor, similar functional assays are carried out with a human embryonic kidney cell line stably expressing the human "ganglionic subtype" or a cell line endogenously expressing the human "muscle type" of nicotinic receptors.

In the last 12 years much effort has been focused on developing selective α7 nAChR positive allosteric modulators leading to the discovery of many different chemotypes displaying said selective activity. These efforts are summarized the review from Haydar et al (Current Topics in Medicinal Chemistry, 2010, 10, 144-152), which describes 11 compounds acting as α7 nAChR positive allosteric modulators belonging to seven different chemical families; i.e. XY-4083; PNU-120596, PHA-758454 and NS-1738; PHA-709829; SB-206553; LY-2087101, LY-1078733 and LY-2087133; compound 26; and A-867744 (compound designations taken from Haydar et al). All said 11 compounds described in Haydar et al are incorporated herein by reference. In fact, at least one drug candidate having an α7 nAChR positive allosteric modulator mode of action obtained permission from the U.S. Food and Drug Administration to conduct clinical testing (i.e. XY-4083).

In one embodiment, the α7-nAChR positive allosteric modulator is a compound selected from the Group P4; Group P4 is the group consisting of compounds F-1: (Z)—N-(4-Chloro-phenyl)-3-(4-chloro-phenylamino)-2-(3-methyl-isoxazol-5-yl)-acrylamide (XY-4083);
F-2: 1-(5-Chloro-2,4-dimethoxy-phenyl)-3-(5-methyl-isoxazol-3-yl)-urea (PNU-120596);
F-3: 1-(5-Fluoro-2,4-dimethoxy-phenyl)-3-(5-trifluoromethyl-isoxazol-3-yl)-urea (PHA-758454);
F-4: 1-(5-Chloro-2-hydroxy-phenyl)-3-(2-chloro-5-trifluoromethyl-phenyl)-urea (NS-1738);
F-5: 4-(4-Chloro-phenyl)-2-(4-methoxy-phenyl)-5-methyl-2H-pyrazol-3-ylamine (PHA-709829);
F-6: 5-Methyl-3,5-dihydro-2H-pyrrolo[2,3-f]indole-1-carboxylic acid pyridin-3-ylamide (SB-206553);
F-7: [2-(4-Fluoro-phenylamino)-4-methyl-thiazol-5-yl]-thiophen-3-yl-methanone (LY-2087101);
F-8: [2-(4-Fluoro-phenylamino)-4-methyl-thiazol-5-yl]-p-tolyl-methanone (LY-1078733);
F-9: Benzo[1,3]dioxol-5-yl-[2-(4-fluoro-phenylamino)-4-methyl-thiazol-5-yl]-methanone (LY-2087133);
F-10: 4-Naphthalen-1-yl-3a,4,5,9b-tetrahydro-3H-cyclopenta[c]quinoline-8-sulfonic acid amide; and
F-11: 4-[5-(4-Chloro-phenyl)-2-methyl-3-propionyl-pyrrol-1-yl]-benzenesulfonamide (A-867744);

wherein said compound is in free base form or in acid addition salt form.

A further aspect of the invention concerns the use of a α7-nAChR positive allosteric modulator for the treatment (whether therapeutic or prophylactic), prevention or delay of progression of dyskinesia associated with dopamine agonist therapy in Parkinson's Disease; wherein said α7-nAChR positive allosteric modulator is a compound selected from the Group P4.

A further aspect of the invention relates to a method for the treatment, prevention or delay of progression of dyskinesia associated with dopamine agonist therapy in Parkinson's Disease in a subject in need of such treatment, which comprises administering to said subject a therapeutically effective amount of a α7-nAChR positive allosteric modulator; wherein said α7-nAChR positive allosteric modulator is a compound selected from the Group P4.

A further aspect of the invention relates to a method for the treatment, prevention or delay of progression of dyskinesia associated with dopamine agonist therapy in Parkinson's Disease in a subject in need of such treatment, which comprises (i) diagnosing dyskinesia associated with dopamine agonist therapy in Parkinson's Disease in said subject and (ii) administering to said subject a therapeutically effective amount of a α7-nAChR positive allosteric modulator; wherein said α7-nAChR positive allosteric modulator is a compound selected from the Group P4.

A further aspect of the invention relates to a pharmaceutical composition comprising a α7-nAChR positive allosteric modulator for the treatment, prevention or delay of progression of dyskinesia associated with dopamine agonist therapy in Parkinson's Disease; wherein said α7-nAChR positive allosteric modulator is a compound selected from the Group P4.

A further aspect of the invention relates to the use of a α7-nAChR positive allosteric modulator for the manufacture of a medicament for the treatment, prevention or delay of progression of dyskinesia associated with dopamine agonist therapy in Parkinson's Disease; wherein said α7-nAChR positive allosteric modulator is a compound selected from the Group P4.

The acid addition salt of α7-nAChR agonists or α7-nAChR positive allosteric modulators are preferably pharmaceutically acceptable salts. Such salts are known in the field (e.g. S. M. Berge, et al, "Pharmaceutical Salts", J. Pharm. Sd., 1977, 66:1-19; and "Handbook of Pharmaceutical Salts, Properties, Selection, and Use", Stahl, R H., Wermuth, C. G., Eds.; Wiley-VCH and VHCA: Zurich, 2002). A "pharmaceutically acceptable salt" is intended to mean a salt of a free base of a α7-nAChR agonist or α7-nAChR positive allosteric modulator that is not toxic, biologically intolerable, or otherwise biologically undesirable. Preferred pharmaceutically acceptable salts are those that are pharmacologically effective and suitable for contact with the tissues of patients without undue toxicity, irritation, or allergic response.

Dyskinesia Associated with Dopamine Agonist Therapy:

"Dopamine agonist therapy" is generally used in the treatment of Parkinson's Disease.

The term "dopamine agonist therapy" as used herein, unless indicated otherwise, means any therapy that increases dopamine receptor stimulation, including, but not limited to, therapies that directly stimulate dopamine receptors (such as administration of bromocriptine) and therapies that increase the levels of dopamine (such as administration of levodopa or of drugs which inhibit dopamine metabolism).

Dopamine agonist therapies include, but are not limited to, therapies which comprise the administration of one or more of the following agents:
levodopa (or L-dopa being a precursor of dopamine);
levodopa in combination with a levodopa decarboxylase inhibitor, such as carbidopa or benserazide;
levodopa in combination with a catechol-O-methyl transferase inhibitor, such as tolcapone or entacapone;
a monoamine oxidase B-inhibitor, such as selegiline or rasagiline;
a dopamine receptor agonist, such as bromocriptine, pergolide, pramipexole, ropinirole, cabergoline, apomorphine or lisuride.

The term "dopamine agonist" as used herein, unless otherwise indicated, means any agent that increases dopamine receptor stimulation. Preferred dopamine agonists are levodopa; levodopa in combination with a levodopa decarboxylase inhibitor; levodopa in combination with a catechol-O-methyl transferase inhibitor; a monoamine oxidase B-inhibitor and a dopamine receptor agonist.

In one embodiment of the invention, the therapy comprises the administration of levodopa. Due to prevalence of associated dyskinesia, the daily dosage of levodopa for an effective dopamine agonist therapy of Parkinson's Disease needs to be determined for each patient individually and ranges typically from 250 to 1500 mg. Said total daily dose is distributed between 2-6 administrations per day, e.g. 3-6 administrations of 50-100 mg per administration. Usually, the daily dosage of levodopa needed for an effective therapy increases during the course of the therapy.

In one embodiment of the invention, the therapy comprises the administration of levodopa in combination with a levodopa decarboxylase inhibitor, such as carbidopa or benserazide.

The term "dyskinesia associated with dopamine agonist therapy", as used herein, unless otherwise indicated, means any dyskinesia which accompanies, or follows in the course of, dopamine agonist therapy, or which is caused by, related to, or exacerbated by dopamine agonist therapy, wherein dyskinesia and dopamine agonist therapy are as defined above. Such dyskinesia often, although not exclusively, occurs as a side-effect of said dopamine agonist therapies of Parkinson's Disease.

Characteristics of such dyskinesias include motor impairment, e.g. the appearance of slow and uncoordinated involuntary movements, shaking, stiffness and problems walking.

For example, patients treated with levodopa often have reduced symptoms of Parkinson's disease but they experience increasing difficulties to remain standing or even sitting. After prolonged use of levodopa, a majority of patients develop such dyskinesia. Dyskinesia can occur at any time during the cycle of treatment with levodopa.

In one embodiment, the α7-nAChR agonists or α7-nAChR positive allosteric modulators are for the treatment of dyskinesia, wherein the therapy comprises administration of levodopa, and said dyskinesia occurs at the time of peak levodopa plasma concentrations in the patient.

In one embodiment, the α7-nAChR agonists or α7-nAChR positive allosteric modulators are for the treatment of dyskinesia, wherein the therapy comprises administration of levodopa, and said dyskinesia occurs when the levodopa plasma concentrations in a patient rise or fall (diphasic dyskinesia).

Surprisingly it was found that α7-nAChR agonists and/or positive allosteric modulators are able to prolong the action of dopamine agonists, e.g. levodopa. Consequently, compared to therapies using such dopamine agonists, the time interval for administration of said dopamine agonists may be prolonged leading to a lower daily dosage needed to achieve equal control of Parkinson's Disease.

A further aspect of the invention relates to a method for the treatment or delay of progression of Parkinson's Disease in a subject in need of such treatment, which comprises administering to said subject a therapeutically effective amount of (i) a dopamine agonist and (ii) a α7-nAChR agonist or a α7-nAChR positive allosteric modulator, wherein the daily dosage of the dopamine agonist is reduced compared to the daily dosage of said dopamine agonist needed to reach an equal control of Parkinson's Disease in the subject without co-administration of the α7-nAChR agonist or the α7-nAChR positive allosteric modulator.

In a preferred embodiment, said dopamine agonist comprises levodopa. In a further preferred embodiment, said reduced daily dosage is a dosage reduced by at least 10%. In a further preferred embodiment, said reduced daily dosage is a dosage reduced by at least 20%. In a further preferred embodiment, said reduced daily dosage is achieved by administering the dopamine agonist in larger time intervals.

Treatment may comprise a reduction in the characteristics associated with dyskinesia, including for example, although not limited to, a reduction in the scale of involuntary movements, a reduction in the number of involuntary movements, an improvement in the ability to carry out normal tasks, an improved ability to walk, increased period of time between episodes of dyskinesia.

One aspect of the treatment of dyskinesias associated with dopamine agonist therapy in Parkinson's Disease is that said treatment should have a minimal adverse effect on the treatment of Parkinson's Disease itself, which is effected by the dopamine agonist therapy. For example: neuroleptics, which can be used to treat dyskinesias, have an adverse effect on the efficiency of the dopamine agonist therapy, for example in parameters associated with cognition, depression and sleep behavior of Parkinson's Disease patients. Highly relevant would be an anti-dyskinetic agent that has a positive effect on the treatment of Parkinson's Disease itself, e.g. improving parameters associated with cognition.

In the case of prophylactic treatment, the α7-nAChR agonists or α7-nAChR positive allosteric modulators may be used to delay or prevent the onset of dyskinesia.

The term "subject" as used herein refers preferably to a human being, especially to a patient being diagnosed with Parkinson's Disease.

The term "therapeutically effective amount" as used herein typically refers to a drug amount which, when administered to a subject, is sufficient to provide a therapeutic benefit, e.g. is sufficient for treating, preventing or delaying the progression of dyskinesias associated with dopamine agonist therapy (e.g. the amount provides an amelioration of symptoms, e.g. it leads to a reduction in the scale of involuntary movements).

For the above-mentioned indications (the conditions and disorders) the appropriate dosage will vary depending upon, for example, the compound employed, the host, the mode of administration and the nature and severity of the condition being treated. However, in general, satisfactory results in animals are indicated to be obtained at a daily dosage of from about 0.01 to about 100 mg/kg body weight, preferably from about 0.1 to about 10 mg/kg body weight, e.g. 1 mg/kg. In larger mammals, for example humans, an indicated daily dosage is in the range from about 0.1 to about 1000 mg, preferably from about 1 to about 400 mg, most preferably from about 3 to about 100 mg of a α7-nAChR agonist or a α7-nAChR positive allosteric modulator conveniently administered, for example, in divided doses up to four times a day.

Pharmaceutical Compositions:

For use according to the invention, the α7-nAChR agonist or α7-nAChR positive allosteric modulator may be administered as single active agent or in combination with other active agents, in any usual manner, e.g. orally, for example in the form of tablets or capsules, parenterally, for example in the form of injection solutions or suspensions, or transdermally, for example in the form of a patch.

In one embodiment, the manner of administration is oral administration, for example in the form of tablets or capsules.

In one embodiment, the manner of administration is transdermal administration, for example in the form of a patch.

Moreover, the present invention provides a pharmaceutical composition comprising a α7-nAChR agonist or α7-nAChR positive allosteric modulator in association with at least one pharmaceutical carrier or diluent for the treatment, prevention or delay of progression of dyskinesia associated with dopamine agonist therapy in Parkinson's Disease. Such compositions may be manufactured in conventional manner. Unit dosage forms may contain, for example, from about 2.5 to about 25 mg of one or more of the α7-nAChR agonist or α7-nAChR positive allosteric modulator.

The pharmaceutical compositions according to the invention are compositions for enteral, such as nasal, rectal or oral; parenteral, such as intramuscular or intravenous; or transdermal (e.g. by a patch) administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilizing, mixing, granulating or confectioning processes. Such processes are exemplified in WO 2005/079802, WO 2003/047581, WO 2004/000316, WO 2005/044265, WO 2005/044266, WO 2005/044267, WO 2006/114262 and WO 2007/071358.

Compositions for transdermal administration are described in Remington's Pharmaceutical Sciences 16$^{th}$ Edition Mack; Sucker, Fuchs and Spieser, Pharmazeutische Technologie, 1$^{st}$ Edition, Springer.

Combinations:

The invention also provides a combination comprising (A) a α7-nAChR agonist or α7-nAChR positive allosteric modulator; and (B) at least one of levodopa, a levodopa decarboxylase inhibitor, a catechol-O-methyl transferase inhibitor, a monoamine oxidase B-inhibitor or a dopamine receptor agonist.

A further aspect of the invention concerns a combination comprising (A) a α7-nAChR agonist; and (B) at least one of levodopa, a levodopa decarboxylase inhibitor, a catechol-O-methyl transferase inhibitor, a monoamine oxidase B-inhibitor or a dopamine receptor agonist; wherein said α7-nAChR agonist is a compound of formula (I).

A further aspect of the invention concerns a combination comprising (A) a α7-nAChR agonist; and (B) at least one of levodopa, a levodopa decarboxylase inhibitor, a catechol-O-methyl transferase inhibitor, a monoamine oxidase B-inhibitor or a dopamine receptor agonist; wherein said α7-nAChR agonist is a compound selected from the Group P1.

A further aspect of the invention concerns a combination comprising (A) a α7-nAChR agonist; and (B) at least one of levodopa, a levodopa decarboxylase inhibitor, a catechol-O-methyl transferase inhibitor, a monoamine oxidase B-inhibitor or a dopamine receptor agonist; wherein said α7-nAChR agonist is a compound selected from the Group P2.

A further aspect of the invention concerns a combination comprising (A) a α7-nAChR agonist; and (B) at least one of levodopa, a levodopa decarboxylase inhibitor, a catechol-O-methyl transferase inhibitor, a monoamine oxidase B-inhibitor or a dopamine receptor agonist; wherein said α7-nAChR agonist is a compound selected from the Group P3.

Preferably, the combination is a pharmaceutical composition or a combined pharmaceutical preparation.

In this pharmaceutical composition, the combination partners i.e.
(A) the α7-nAChR agonist or the α7-nAChR positive allosteric modulator, and
(B) at least one of
i) levodopa, or
ii) a dopa decarboxylase inhibitor, or
iii) a catechol-O-methyl transferase inhibitor, or
iv) a monoamine oxidase B-inhibitor, or
iv) a dopamine agonist
can be administered together, one after the other or separately in one combined unit dosage form or in two separate unit dosage forms. The unit dosage form may also be a fixed combination.

As used herein, the term "combinations" shall be taken to mean one or more substances which can be administered together, one after the other or separately in one combined unit dosage form or in two separate unit dosage forms.

Administration of the dosage forms may be co-cominantly, simultaneously, part-simultaneously, separately or sequentially. The dosage forms of the combination may not necessarily be of the same dosage form and may comprise one or more of:
Enteral: Oral (capsule, tablet, solution), Rectal (suppository)
Parenteral: Intravenous injection, subcutaneous injection, intramuscular injection,
intraperitoneal injection, intramammary injection
Respiratory: Inhalation, Intranasal, Intratracheal
Topical: Mucous membrane application, skin application.

In addition, the release profiles of the medicaments may not be the same, for example one or more component of the combination may be of extended release form.

In one embodiment of the invention a specific combination is used. Said combination comprises:

(A) a α7-nAChR agonist or a α7-nAChR positive allosteric modulator; and
(B) at least one active agent selected from the group consisting of levodopa, carbidopa, benserazide tolcapone, entacapone, bromocriptine, pergolide, pramipexole, ropinirole, cabergoline, apomorphine and lisuride.

A further aspect of the invention concerns a combination comprising: (A) a α7-nAChR agonist; and (B) at least one active agent selected from the group consisting of levodopa, carbidopa, benserazide tolcapone, entacapone, bromocriptine, pergolide, pramipexole, ropinirole, cabergoline, apomorphine and lisuride; wherein said α7-nAChR agonist is a compound of formula (I).

A further aspect of the invention concerns a combination comprising: (A) a α7-nAChR agonist; and (B) at least one active agent selected from the group consisting of levodopa, carbidopa, benserazide tolcapone, entacapone, bromocriptine, pergolide, pramipexole, ropinirole, cabergoline, apomorphine and lisuride; wherein said α7-nAChR agonist is a compound selected from the Group P1.

A further aspect of the invention concerns a combination comprising: (A) a α7-nAChR agonist; and (B) at least one active agent selected from the group consisting of levodopa, carbidopa, benserazide tolcapone, entacapone, bromocriptine, pergolide, pramipexole, ropinirole, cabergoline, apomorphine and lisuride; wherein said α7-nAChR agonist is a compound selected from the Group P2.

A further aspect of the invention concerns a combination comprising: (A) a α7-nAChR agonist; and (B) at least one active agent selected from the group consisting of levodopa, carbidopa, benserazide tolcapone, entacapone, bromocriptine, pergolide, pramipexole, ropinirole, cabergoline, apomorphine and lisuride; wherein said α7-nAChR agonist is a compound selected from the Group P3.

In one embodiment of the invention a specific combination is used. Said combination comprises:
(A) a α7-nAChR agonist or a α7-nAChR positive allosteric modulator; and
(B) levodopa and at least one active agent selected from the group consisting of carbidopa,
benserazide tolcapone, entacapone, bromocriptine, pergolide, pramipexole, ropinirole, cabergoline, apomorphine or lisuride.

An example of said embodiment is a combination of a α7-nAChR agonist or a α7-nAChR positive allosteric modulator with levodopa which may further comprise a levodopa decarboxylase inhibitor, such as carbidopa or benserazide.

An example of said embodiment is a combination of a α7-nAChR agonist selected from the Group P3 with levodopa which further comprises a levodopa decarboxylase inhibitor, such as carbidopa.

An example of said embodiment is a combination of a α7-nAChR agonist selected from the Group P3 with levodopa which further comprises a levodopa decarboxylase inhibitor, such as benserazide.

In one embodiment of the invention a specific combination is used. Said combination comprises:
(A) a α7-nAChR agonist or a α7-nAChR positive allosteric modulator; and
(B) levodopa; carbidopa and entacapone.

An example of said embodiment is a combination of a α7-nAChR agonist or a α7-nAChR positive allosteric modulator with STALEVO® (carbidopa, levodopa and entacapone) tablets (STALEVO® is a registered trademark of Orion Corporation, Espoo, Finland).

An example of said embodiment is a combination of a α7-nAChR agonist selected from the Group P3 with STALEVO® (carbidopa, levodopa and entacapone) tablets.

The invention also provides a product, for example a kit, comprising a α7-nAChR agonist or α7-nAChR positive allosteric modulator and levodopa as a combined preparation for simultaneous, separate or sequential use in therapy. The product may further comprise a levodopa decarboxylase inhibitor, such as carbidopa or benserazide.

EXAMPLES

The usefulness of the α7-nAChR agonists or α7-nAChR positive allosteric modulators in the treatment of the above-mentioned disorders can be confirmed in a range of standard tests including those indicated below.
1. In-Vitro Tests
1.1. Selectivity of Selected α7-nAChR Agonists Against α4β2-nAChR Based on the activity/selectivity data shown below it is concluded that said compounds are selective agonists at the α7-nAChR.

| Compound | α7-nAChR activity | | α4β2-nAChR activity | | fold selectivity |
|---|---|---|---|---|---|
| | Potency $EC_{50}$ (nM) | Efficacy compared to epibatidine (100%) | $IC_{50}$ (nM) | $EC_{50}$ (nM) | |
| A-1 | 100 | 83 | 23442 | >100 000 | 234 |
| C-1 | 24 | 84 | 9333 | >100 000 | 388 |
| B-13 | 13 | 89 | 4217 | >100 000 | 324 |

Assay:
To assess α7-nAChR activity, a functional assay was employed using GH3 cells that recombinantly expressed human α7-nAChR. 50000 cells per well were seeded 72 h prior to the experiment on black 96-well plates (Costar) and incubated at 37° C. in a humidified atmosphere (5% $CO_2$/95% air). On the day of the experiment, medium was removed by flicking the plates and replaced with 100 µl growth medium containing 2 mM Fluo-4, (Molecular Probes) in the presence of 2.5 mM probenecid (Sigma). The cells were incubated at 37° C. in a humidified atmosphere (5% CO2/95% air) for 1 h. Plates were flicked to remove excess of Fluo-4, washed twice with Hepes-buffered salt solution (in mM: NaCl 130, KCl 5.4, CaCl2 2, MgSO4 0.8, NaH2PO4 0.9, glucose 25, Hepes 20, pH 7.4; HBS) and refilled with 100 µl of HBS containing antagonist when appropriate. The incubation in the presence of the antagonist lasted 3-5 minutes. Plates were placed in the cell plate stage of a FLIPR device (fluorescent imaging plate reader, Molecular Devices, Sunnyvale, Calif., USA). After recording of the baseline (laser: excitation 488 nm at 1 W, CCD camera opening of 0.4 seconds) the agonists (50 µl) were added to the cell plate using the FLIPR 96-tip pipettor while simultaneously recording the fluorescence.

Calcium kinetic data were normalized to the maximal fitted response induced by epibatidine, which is a full agonist at α7-nAChR. Four parameter Hill equations were fitted to the concentration-response. Values of Emax (maximal effect in % compared to the epibatidine response) and EC50 (concentration producing half the maximal effect in µM) were derived from this fit.

Assay Described in:
D Feuerbach et al, Neuropharmacology (2005), 48, 215-227.

To assess the activity of the compound of the invention on the human neuronal nAChR α4β2, a similar functional assay is carried out using a human epithelial cell line stably expressing the human α4β2 subtype (Michelmore et al., Naunyn-Schmiedeberg's Arch. Pharmacol. (2002) 366, 235).

2. In-Vivo Preclinical Tests
2.1. Oral Bioavailability and Brain Penetration in Mice Based on the pharmacokinetic data shown below it is concluded that the brain concentration of said compounds in mice is beyond (or at least equal) to the compound's $EC_{50}$ at the α7-nAChR for at least 4 hours following an acute oral dose of 30 µmol/kg.

Compound A-1:

| Administration | Time (hour) | Plasma (pmoles/ml ± SD) | Brain (pmoles/g ± SD) | Ratio Brain/plasma |
|---|---|---|---|---|
| 30 µmol/kg p.o. | 0.5 | 634.9 ± 261.3 | 706.3 ± 153.4 | 1.1 |
| 30 µmol/kg p.o. | 1 | 684.7 ± 339.6 | 573.7 ± 109.3 | 0.8 |
| 30 µmol/kg p.o. | 2 | 168.2 ± 91.3 | 191.9 ± 34.9 | 1.1 |
| 30 µmol/kg p.o. | 4 | 85.0 ± 54.3 | 104.6 ± 39.6 | 1.2 |
| 30 µmol/kg p.o. | 6 | 29.5 ± 13.8 | 40.5 ± 12.1 | 1.4 |
| 30 µmol/kg p.o. | 24 | 3.8 ± 0.6 | 9.1 ± 2.7 | 2.4 |

Compound B-13:

| Administration | Time (hour) | Plasma (pmoles/ml ± SD) | Brain (pmoles/g ± SD) | Ratio Brain/plasma |
|---|---|---|---|---|
| 30 µmol/kg p.o. | 0.25 | 2196 ± 397 | 1884 ± 291 | 0.86 |
| 30 µmol/kg p.o. | 0.5 | 2265 ± 419 | 2960 ± 706 | 1.31 |
| 30 µmol/kg p.o. | 1 | 1554 ± 523 | 2940 ± 335 | 1.89 |
| 30 µmol/kg p.o. | 2 | 1172 ± 252 | 1260 ± 172 | 1.07 |
| 30 µmol/kg p.o. | 4 | 429 ± 167 | 379 ± 134 | 0.88 |
| 30 µmol/kg p.o. | 8 | 80 ± 23 | 93 ± 30 | 1.17 |
| 30 µmol/kg p.o. | 24 | * | 13 ± 4 | |

Compound C-1:

| Administration | Time (hour) | Plasma (pmoles/ml ± SD) | Brain (pmoles/g ± SD) | Ratio Brain/plasma |
|---|---|---|---|---|
| 30 µmol/kg p.o. | 0.25 | 1601 ± 758 | 620 ± 221 | 0.39 |
| 30 µmol/kg p.o. | 0.5 | 3414 ± 956 | 1405 ± 539 | 0.41 |
| 30 µmol/kg p.o. | 1 | 1241 ± 583 | 1458 ± 189 | 1.17 |
| 30 µmol/kg p.o. | 2 | 875 ± 261 | 1478 ± 259 | 1.69 |
| 30 µmol/kg p.o. | 4 | 762 ± 159 | 842 ± 187 | 1.11 |
| 30 µmol/kg p.o. | 8 | 239 ± 27 | 362 ± 62 | 1.51 |
| 30 µmol/kg p.o. | 24 | * | * | |

Assay:

Compounds were orally (30 µmol/kg) administered. Male mice (30-35 g, OF1/ICstrain) were sacrificed at indicated time points after oral administration. Trunk-blood was collected in EDTA-containing tubes and the brain was removed and immediately frozen on dry ice.

To 100 µl plasma 10 µl internal standard (1.0 µmol of a compound with solubility and ionization properties similar to test compounds) was added and extracted three times with 500 µl dichloromethane. The combined extracts were then dried under a stream of nitrogen and re-dissolved in 100 µl acetonitrile/water (70% acetonitrile). Brains were weighed and homogenized in water (1:5 w/v). Two 100 µl aliquots of each homogenate+10 µl of internal standard (same standard as used for the plasma samples) were extracted three times with 500 µl dichloromethane and further processed as the plasma samples. Samples were separated on Beckmann high-performance liquid chromatography equipment system with an autosampler (Gilson 233XL). A 10 min linear gradient (10-70%) of acetonitrile containing 0.5% (v/v) formic acid was used to elute the compounds from Nucleosil CC-125/2 C18 reversed phase (Machery&Nagel) column.

The limit of detection (LOD), defined as the lowest concentration of the extracted standard sample with a signal to noise ratio of ~3.

2.2. Functional Read-Out in Mice (Social Recognition Test)

Based on the functional in-vivo data shown below it is concluded that oral dosing of said compounds at relevant concentrations lead to a specific effect associated with α7-nAChR (i.e. cognition enhancement in the Social Recognition Test in mouse).

| Compound | Reduction in time scrutinizing in % ± SEM at 24 h | Dose in mg/kg |
|---|---|---|
| A-1 | 52 ± 4 | 3 |
| C-1 | 51 ± 3 | 0.3 |
| B-13 | 37 ± 7 | 0.3 |

Assay:

Social interactions between two experimental animals are influenced by their degree of familiarity: the better they know each other, the less time they spend on mutual scrutiny at each meeting. In agreement with published data in rats (Mondadori et al., 1993) we have observed (i) that an adult mouse shows a shortened scrutiny of a young conspecific if the two mice are brought together again within a short time interval (e.g. 1 hour), (ii) that this curtailment is attributable to memory processes: it does not occur if the familiar young partner is replaced by a strange (unfamiliar) young mouse on the second occasion and (iii) that the adult mouse's recollection of the previously scrutinized juvenile partner fades with the elapsed time, i.e., after 24 h, scrutiny takes just about as long as at the first encounter. Memory enhancing agents (i.e. oxiracetam) facilitate learning to the extent that the previously met (familiar) partner is still remembered after 24 h, whereas in vehicle treated control animals the memory usually fades after less than 1 hour (Thor and Holloway, 1982) or after 2-3 hours.

Baseline-Test:

Pairs consisting of one adult and one young mouse were assigned at random to the experimental and control groups. In each pair only the adult mouse was orally treated 1 hour before the trial with either vehicle or the test compound. The duration of active contacts of the adult mouse with the young mouse was manually recorded over a period of 3 min, including the following behavioural, approach-related items: sniffing, nosing, grooming, licking, pawing and playing, anogenital exploration and orientation toward the young mouse; orientation, thereby, was defined as tip of nose of the adult mouse less than approximately 1 cm distant from the young mouse's body.

Re-Test:

Twenty-four hours after the baseline-test, the adults in each treatment group were confronted again with the previously encountered (familiar) partner, whereas the half of the adult animals were put together with the previously encountered (familiar) partner and the other half with another (unfamiliar) young mouse. Again the duration of active approach-behaviours was recorded during a 3-min period. Prior to re-test no oral injection was given.

In the table the reduction in time scrutinizing the familiar partner at time 24 compared with the familiar partner at time 0 minutes is given (value of zero would signify no reduction).

2.3. Assessment of Antidyskinetic Effect in Parkinsonian Primates

Based on the in-vivo data in parkinsonian primates shown below it is concluded that compound A-1 does not delay the onset of action of levodopa, does not lower the antiparkinsonian activity of levodopa, significantly reduces the levodopa-induced dyskinesias and significantly increases the duration of the antiparkinsonian activity of levodopa.

2.3.1 Method

Female ovariectomized cynomolgus monkeys (*Macaca fascicularis*) are used in the assessment. The animals can be rendered parkinsonian by continuous infusion of 1-methyl-4-phenyl-1,2,3,6-tetrahydropyridine (MPTP) until they develop a stable parkinsonian syndrome. After recuperation, animals are treated daily with levodopa until clear and reproducible dyskinesias are developed.

2.3.2 Assessment

Monkeys are observed through a one-way screen window in their home cage. They are observed and scored repeatedly at baseline and after a standard s.c. dose of levodopa. Locomotor activity is assessed and followed with an electronic monitoring system. Antiparkinsonian responses are evaluated by measuring the locomotor activity and a Parkinson disability scale (see Hadj Tahar A et al, Clin Neuropharmacol 2000; 23:195-202; and Samadi P et al, Neuropharmacology 2003; 45:954-963). Dyskinesias are closely monitored and scored according to a dyskinesia rating scale (also described in Hadj Tahar A et al; and Samadi P et al) every 15 minutes until the end of the effect. The doses of levodopa are chosen to induce motor activation and reproducible dyskinesia but no excessive agitation.

2.3.3 Protocol

Monkeys are observed for at least two hours following an oral administration of vehicle. On a subsequent day, the dose of levodopa selected is tested once. The animals are observed (with measures of parkinsonian and dyskinetic scores) for the entire duration of the levodopa effect and are also monitored for locomotor activity. This provides vehicle control values as well as levodopa antiparkinsonian and dyskinesia response data for comparison with combinations of a α7-nAChR agonist/positive allosteric modulator and levodopa. The monkeys are then tested with a α7-nAChR agonist/positive allosteric modulator in combination with a fixed dose of levodopa. A suspension for oral administration of the α7-nAChR agonist/positive allosteric modulator is administered before levodopa. After each dose, the animals are observed (with measures of parkinsonian and dyskinetic scores) for the entire duration of effect and monitored for locomotor activity or any change in behavior (e.g. circling, excitement, lethargy and sleepiness).

Using this protocol, compound A-1 at a dose of 20 mg/kg was tested. Results based on five monkeys (levodopa/benserazide doses: 22.5/50 mg; 65/50 mg; 30/50 mg; 35/50 mg; and 25/50 mg) are shown in FIGS. 1-4. In said experiments, compound A-1 reduced the Mean Dyskinesia Score (total period) from 2.8 to 2.1; furthermore, compound A-1 extended the Duration of Levodopa-Response from 230 minutes to 265 minutes. Neither Elapsed Time after Levodopa Administration or extent of the antiparkinsonian activity of Levodopa measured with the antiparkinsonian score were changed significantly with the addition of compound A-1.

2. Clinical Testing: Improvement Trials

Clinical testing of the α7-nAChR agonist/positive allosteric modulator may be conducted, for example, in one of the following study designs. The skilled physician may look at a number of aspects of patient behaviors and abilities. He will realize that such studies are considered as guidelines and the certain aspects of the studies may be modified and redefined depending on the circumstance and environment, for example.

2.1 Trial A: Normal Patient Population

A patient population, with a normal control is dosed once a day for a week or longer tested. The test is designed to allow for improvement, i.e. that there is a measurable parameter increase of the impaired function The patients are tested at the beginning and at the end of the dosage period and the results are compared and analyzed.

2.2 Trial B: Deficit Population

A patient population with a deficit associated with Parkinson's Disease and associated disorders e.g. Parkinson's dyskinesia, for example, Parkinson's Disease levodopa induced Parkinson's dyskinesia is dosed once a day for a week or longer and tested. The test is designed to allow for improvement, I.e. that there is a measurable parameter increase of the impaired function. The patients are tested at the beginning and at the end of the dosage period and the results are compared and analyzed.

2.3 Considerations for Designing a Trial

When designing a trial, the skilled person will appreciate the need to protect both against floor and ceiling effects. In other words, the study designing should allow cognition to the measurably raised or lowered.

Conditions that artificially impair a function, e.g. cognition, are one way to test enhancement of that function. Such conditions are, for example, sleep deprivation and pharmacological challenges.

Placebo control is required for all trials.

In assessing the data, evaluation of the likelihood of learning and practice effects from repeat assessments must be made. The likelihood of such effects contaminating the data to produce false positives should be taken in to account when designing the test, e.g. the tests should not be identical (e.g. commit the same list of words to memory) but designed to study the same mechanism. Other countermeasures may include single testing at the end of a trial only.

EMBODIMENTS

In addition to other illustrative embodiments, this invention can be seen to comprise one or more of the following illustrative embodiments:

1. A nicotinic acetylcholine receptor alpha 7 agonist or a nicotinic acetylcholine receptor alpha 7 positive allosteric modulator for use in the treatment, prevention or delay of progression of dyskinesia associated with dopamine agonist therapy in Parkinson's Disease.

2. A nicotinic acetylcholine receptor alpha 7 agonist for use in the treatment, prevention or delay of progression of dyskinesia associated with dopamine agonist therapy in Parkinson's Disease.

3. A compound according to any of embodiments 1 or 2, wherein the therapy comprises the administration of levodopa.

4. A method for the treatment, prevention or delay of progression of dyskinesia associated with dopamine agonist therapy in Parkinson's Disease in a subject in need of such treatment, which comprises administering to said subject a therapeutically effective amount of a nicotinic acetylcholine receptor alpha 7 agonist or a nicotinic acetylcholine receptor alpha 7 positive allosteric modulator.

5. A method for the treatment, prevention or delay of progression of dyskinesia associated with dopamine agonist therapy in Parkinson's Disease in a subject in need of such treatment, which comprises administering to said subject a therapeutically effective amount of a nicotinic acetylcholine receptor alpha 7 agonist.

6. A method according to embodiments 4 or 5, wherein the therapy comprises the administration of levodopa.

7. A method for the treatment or delay of progression of Parkinson's Disease in a subject in need of such treatment, which comprises administering to said subject a therapeutically effective amount of (i) a dopamine agonist and (ii) a α7-nAChR agonist or a α7-nAChR positive allosteric modulator.
wherein the daily dosage of the dopamine agonist is reduced compared to the daily dosage of said dopamine agonist needed to reach an equal control of Parkinson's Disease in the subject without co-administration of the α7-nAChR agonist or the α7-nAChR positive allosteric modulator.

8. A method according to embodiment 7, wherein the dopamine agonist comprises levodopa.

9. A pharmaceutical composition comprising a nicotinic acetylcholine receptor alpha 7 agonist or a nicotinic acetylcholine receptor alpha 7 positive allosteric modulator for the treatment, prevention or delay of progression of dyskinesia associated with dopamine agonist therapy in Parkinson's Disease.

10. A pharmaceutical composition comprising a nicotinic acetylcholine receptor alpha 7 agonist for the treatment, prevention or delay of progression of dyskinesia associated with dopamine agonist therapy in Parkinson's Disease.

11. A composition according to embodiments 9 or 10, wherein the therapy comprises the administration of levodopa.

12. A combination comprising (A) a nicotinic acetylcholine receptor alpha 7 agonist or nicotinic acetylcholine receptor alpha 7 positive allosteric modulator; and (B) at least one of levodopa, a levodopa decarboxylase inhibitor, a catechol-O-methyl transferase inhibitor, a monoamine oxidase B-inhibitor or a dopamine receptor agonist.

13. A combination comprising (A) a nicotinic acetylcholine receptor alpha 7 agonist; and (B) at least one of levodopa, a levodopa decarboxylase inhibitor, a catechol-O-methyl transferase inhibitor, a monoamine oxidase B-inhibitor or a dopamine receptor agonist.

14. A pharmaceutical composition comprising (A) a nicotinic acetylcholine receptor alpha 7 agonist or a nicotinic acetylcholine receptor alpha 7 positive allosteric modulator; and (B) at least one of levodopa, a levodopa decarboxylase inhibitor, a catechol-O-methyl transferase inhibitor, a monoamine oxidase B-inhibitor or a dopamine receptor agonist.

15. A pharmaceutical composition comprising (A) a nicotinic acetylcholine receptor alpha 7 agonist; and (B) at least one of levodopa, a levodopa decarboxylase inhibitor, a catechol-O-methyl transferase inhibitor, a monoamine oxidase B-inhibitor or a dopamine receptor agonist.

We claim:

1. A method for the treatment or delay of progression of a side effect associated with dopamine agonist therapy in Parkinson's Disease in a subject in need of such treatment, wherein the side effect is: motor impairment, an appearance of slow or uncoordinated involuntary movements, shaking, stiffness, or problems walking, comprising:
   administering to said subject a therapeutically effective amount of (R)-3-(6-p-tolyl-pyridin-3-yloxy)-1-aza-bicyclo[2.2.2]octane in free base form or in acid addition salt form.

2. The method of claim 1, wherein treatment results in: a reduction in the scale of involuntary movements, a reduction in the number of involuntary movements, an improvement in ability to carry out normal tasks, an improved ability to walk, or an increased period of time between episodes of dyskinesia.

3. The method of claim 1, wherein the dopamine agonist therapy comprises levodopa.

4. The method of claim 3, wherein the levodopa is administered in an amount that is reduced by at least 10% relative to a daily dosage of 250-1500 mg/day that would be effective for treating a patient not being administered the (R)-3-(6-p-tolyl-pyridin-3-yloxy)-1-aza-bicyclo[2.2.2]octane.

5. The method of claim 4, wherein the levodopa is administered in an amount that is reduced by at least 20% relative to a daily dosage of 250-1500 mg/day that would be effective for treating a patient not being administered the (R)-3-(6-p-tolyl-pyridin-3-yloxy)-1-aza-bicyclo[2.2.2]octane.

6. A method for the treatment or delay of progression of a side effect associated with dopamine agonist therapy in Parkinson's Disease in a subject in need of such treatment, wherein the side effect is: motor impairment, an appearance of slow or uncoordinated involuntary movements, shaking, stiffness, or problems walking, comprising administering to said subject:
   a therapeutically effective amount of (R)-3-(6-p-tolyl-pyridin-3-yloxy)-1-aza-bicyclo[2.2.2]octane in free base form or in acid addition salt form; and
   levodopa, wherein the levodopa is administered in an amount that is reduced by at least 10% relative to a daily dosage of 250-1500 mg/day that would be effective for treating a patient not being administered the therapeutically effective amount of (R)-3-(6-p-tolyl-pyridin-3-yloxy)-1-aza-bicyclo[2.2.2]octane.

* * * * *